(12) United States Patent
Mitra

(10) Patent No.: US 11,559,545 B2
(45) Date of Patent: Jan. 24, 2023

(54) INHIBITION OF UCHL1 IN HIGH-GRADE SEROUS OVARIAN CANCER

(71) Applicant: The Trustees of Indiana University, Indianapolis, IN (US)

(72) Inventor: Sumegha Mitra, Bloomington, IN (US)

(73) Assignee: The Trustees of Indiana University, Bloomington, IN (US)

(*) Notice: Subject to any disclaimer, the term of this patent is extended or adjusted under 35 U.S.C. 154(b) by 337 days.

(21) Appl. No.: 16/774,460

(22) Filed: Jan. 28, 2020

(65) Prior Publication Data

US 2020/0237813 A1 Jul. 30, 2020

Related U.S. Application Data

(60) Provisional application No. 62/798,106, filed on Jan. 29, 2019.

(51) Int. Cl.
*A61K 33/243* (2019.01)
*A61P 35/00* (2006.01)
*C12Q 1/34* (2006.01)

(52) U.S. Cl.
CPC .......... *A61K 33/243* (2019.01); *A61P 35/00* (2018.01); *C12Q 1/34* (2013.01)

(58) Field of Classification Search
None
See application file for complete search history.

(56) References Cited

FOREIGN PATENT DOCUMENTS

WO WO-2017184751 A1 * 10/2017

OTHER PUBLICATIONS

Botestaneanu et al (PLoS One, 2016, 1-19). (Year: 2016).*
Pinckney et al (Applied Cancer Research, 2018, 38:13). (Year: 2018).*

* cited by examiner

*Primary Examiner* — Celeste A Roney
(74) *Attorney, Agent, or Firm* — Taft Stettinius & Hollister LLP

(57) ABSTRACT

In certain aspects, the present disclosure provides methods and materials for the treatment of cancer. In accordance with some forms, the disclosure provides methods for the treatment of cancer which include inhibition of ubiquitin carboxyl-terminal hydrolase.

4 Claims, 29 Drawing Sheets
(6 of 29 Drawing Sheet(s) Filed in Color)

FIG. 7G (Con't)

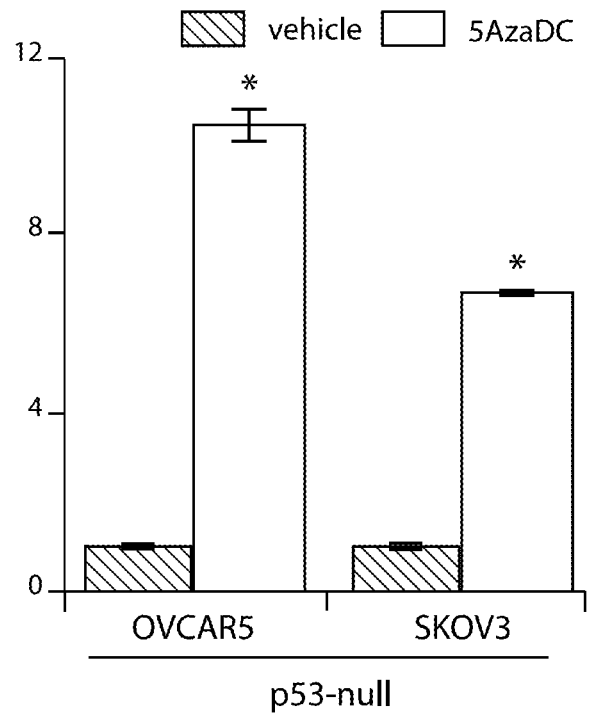
FIG. 7H (Con't)
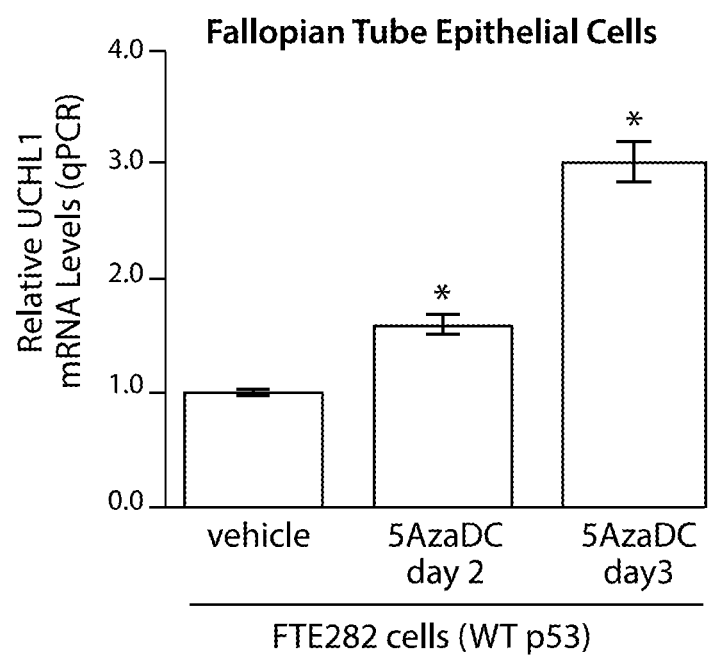
FIG. 7H (Con't)

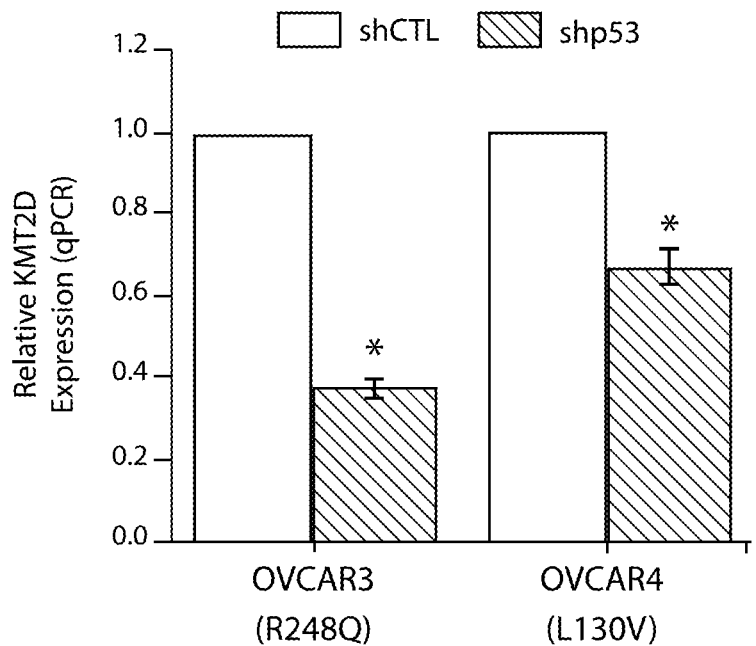
FIG. 7K
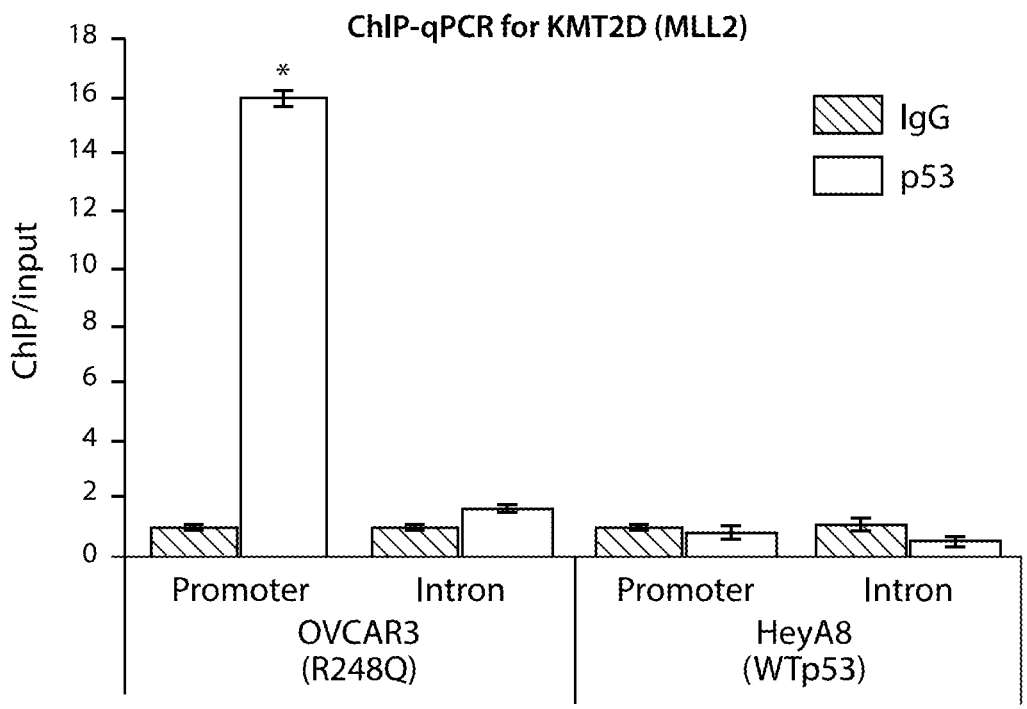
FIG. 7K (Con't)

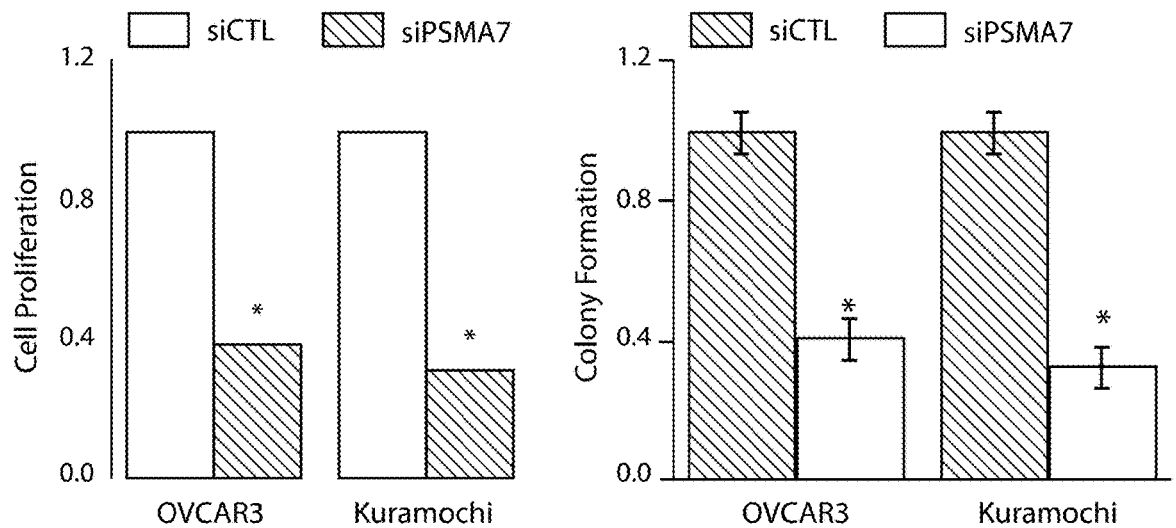
FIG. 9C
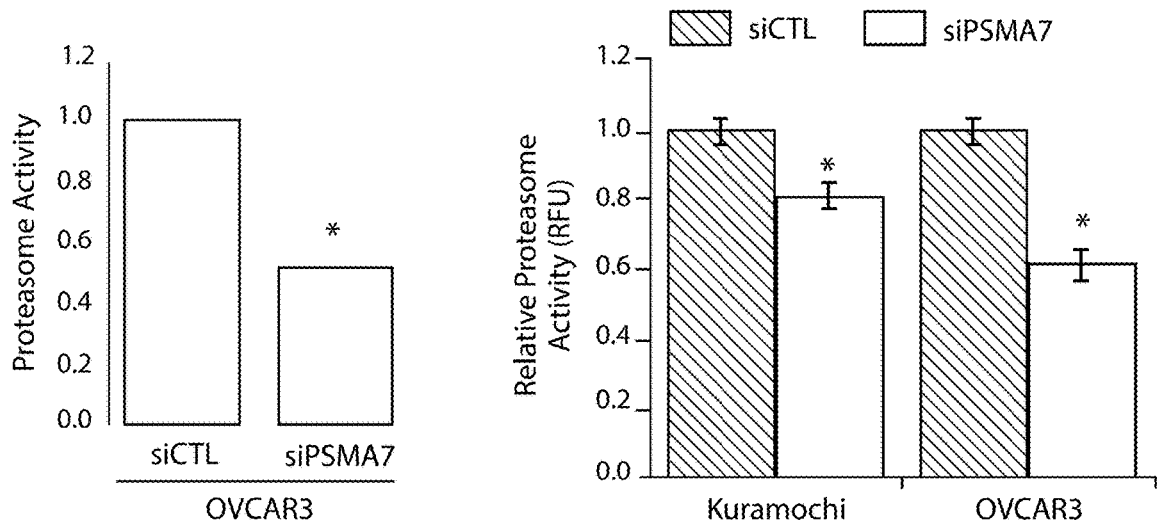
FIG. 9D
FIG. 9E

INHIBITION OF UCHL1 IN HIGH-GRADE SEROUS OVARIAN CANCER

This patent application claims the benefit of, and priority to, U.S. Provisional Patent Application Ser. No. 62/798,106, the disclosure of which is incorporated herein by reference.

BACKGROUND

About 22,440 new cases of ovarian cancer are diagnosed each year in the United States. It is estimated that about 69% of ovarian cancer patients will succumb to the disease. High-grade serous ovarian cancer (HGSOC) is the most lethal and prevalent histotype of ovarian cancer accounting for 70-80% of ovarian cancer deaths. Extensive metastasis and subsequent development of chemo-resistant tumors greatly contributes to the high-mortality rate of HGSOC patients and yet our understanding of the process remains limited.

About 96% of HGSOC patients carry a gain of function mutation in the p53 gene, also known as p53 or the tumor protein. p53 codes for a protein that regulates the cell cycle and hence aides in tumor suppression. p53 proteins have three major functions: growth arrest, DNA repair, and apoptosis. Gain of function p53 mutations are known to orchestrate a distinct pro-tumorigenic signaling network which contributes to extensive metastasis and subsequent development of chemo-resistant tumors. Knowledge of common mechanisms or mediators of oncogenic signaling among different p53 mutants (pan-mutant p53 effect) are critical for better understanding of recurrent disease and identifying novel therapeutic targets. So far there is no drug to limit gain of function mutant p53 oncogenic activity, which contributes to HGSOC metastasis and chemo-resistance.

Ubiquitin carboxyl-terminal hydrolase 1 (UCHL1) is a deubiquitinating enzyme (DUB) from ubiquitin proteasome system (UPS), the major cellular machinery that regulates protein homeostasis. The UPS is responsible for intracellular protein degradation and regulation of many key biological processes, such as transcription regulation, cell cycle control, DNA repair, regulation of cellular signaling, and cell differentiation. UCHL1 is primarily a neuronal and brain protein, which is not widely expressed in normal human tissues. However, UCHL1 is a differentially expressed gene in various cancers, and has been proposed to have oncogenic and/or tumor suppressive properties in various forms of cancer. For example: in breast cancer it is reported as both tumor suppressor and oncogene. This suggests that is role in cancer is not dependent on cellular context. Prior to the present disclosure the role of UCHL1 in high-grade serous ovarian cancer was unknown. Further, high grade serous ovarian cancer lacks novel inhibitors or adjuvants therapies. Thus, there is an urgent and critical need to develop greater understanding of HGSOC mechanisms and novel mediators, which can eventually be translated into novel therapies.

SUMMARY

In certain aspects, the present disclosure provides methods and materials for the treatment of cancer. In accordance with some forms, the disclosure provides methods for the treatment of cancer which include silencing mutant p53-mediated signaling in HGSOC in a patient. Accordingly in one embodiment, the present invention provides a method for treatment of cancer, comprising administering a pharmaceutically effective amount of a therapeutic to a patient with cancer, wherein the therapeutic is effective to silence mutant p53-mediated signaling in HGSOC. In some forms, the therapeutic is effective to silence mutant p53-mediated signaling in HGSOC. In certain embodiments, the cancer comprises ovarian cancer, for example high-grade serous ovarian cancer. In some forms, the cancer comprises a cancer in which ubiquitin carboxyl-terminal hydrolase 1 is over-expressed. In some forms, the patient has a gain of function p53 gene mutation. Certain inventive methods of the present disclosure include the steps of detecting the overexpression of ubiquitin carboxyl-terminal hydrolase 1 and/or the presence of a gain of function p53 gene mutation in the patient.

In another embodiment, the disclosure provides a method for enhancing the effects of a chemotherapeutic agent, comprising administering to a patient a pharmaceutically effective amount of a gene silencing therapeutic in conjunction with the administration of the chemotherapeutic agent. In some forms, the gene silencing therapeutic is effective to silence one or more genes such as p53 and/or MLL2. In certain embodiments, the cancer comprises ovarian cancer, for example high-grade serous ovarian cancer. In some forms, the cancer comprises a cancer in which ubiquitin carboxyl-terminal hydrolase 1 is over-expressed. In some forms, the patient has a gain of function p53 gene mutation. Certain inventive methods of the present disclosure include the steps of detecting the overexpression of ubiquitin carboxyl-terminal hydrolase 1 and/or the presence of a gain of function p53 gene mutation in the patient. In certain embodiments the chemotherapeutic agent comprises an alkylating agent, for example cisplatin.

In another aspect, the disclosure provides for the use of a gene silencing therapeutic for the manufacture of a medicament for treatment of cancer. In some forms, the gene silencing therapeutic is effective to silence mutant p53-mediated signaling in HGSOC. In certain embodiments, the cancer comprises ovarian cancer, for example high-grade serous ovarian cancer. In some forms, the cancer comprises a cancer in which ubiquitin carboxyl-terminal hydrolase 1 is over-expressed. In some forms, the cancer is accompanied by a gain of function p53 gene mutation.

In another embodiment, the disclosure provides a gene silencing therapeutic, for use in the treatment of cancer. In some forms, the gene silencing therapeutic is effective to silence the p53 gene. In certain embodiments, the cancer comprises ovarian cancer, for example high-grade serous ovarian cancer. In some forms, the cancer comprises a cancer in which ubiquitin carboxyl-terminal hydrolase 1 is over-expressed. In some forms, the cancer is accompanied by a gain of function p53 gene mutation.

Additional embodiments, as well as features and advantages of embodiments of the invention, will be apparent from the description herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7K depicts results of TP53 silencing in reducing expression of histone methyltransferase MLL2 in OVCAR3 and OVCAR4 cells with mutant R248Q and L130V p53 mutants respectively. ChIP-qPCR was also performed showing mutant p53 enrichment on MLL2 promoter in OVCAR3 cells.

FIG. 9C depicts a significant reduction in cellular proliferation (5-day) and clonogenicity of PSMA7 silenced OVCAR3 and Kuramochi HGSOC cells compared to unsilenced controls.

FIG. 9D depicts the PSMA7 silenced OVCAR3 cells also demonstrated reduced proteasomal activity.

FIG. 9E depicts a significant decrease in proteasomal activity in PSMA7 silenced Kuramochi and OVCAR3 cells.

The accompanying drawings, which are incorporated herein and constitute part of this specification, illustrate exemplary embodiments of the disclosed patient matter, and together with the general description given above and the detailed description given below, serve to explain the features of the disclosed patient matter.

Figure 12A:
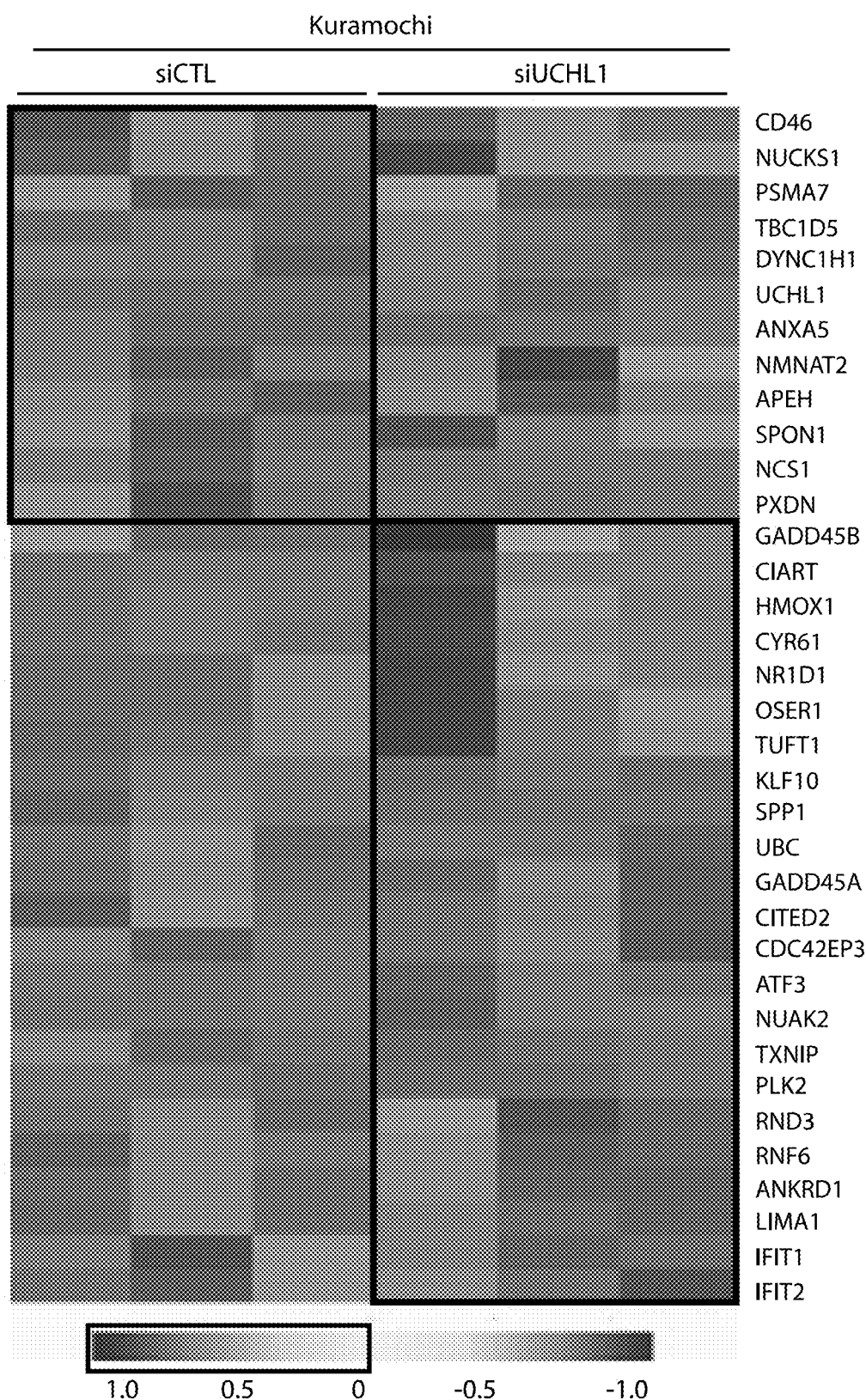

FIG. 12A illustrates the results of RNA-sequencing analysis showing both the upregulated (outlined portion) and downregulated genes in UCHL1 silenced Kuramochi cells compared to unsilenced controls.

Figure 12B:
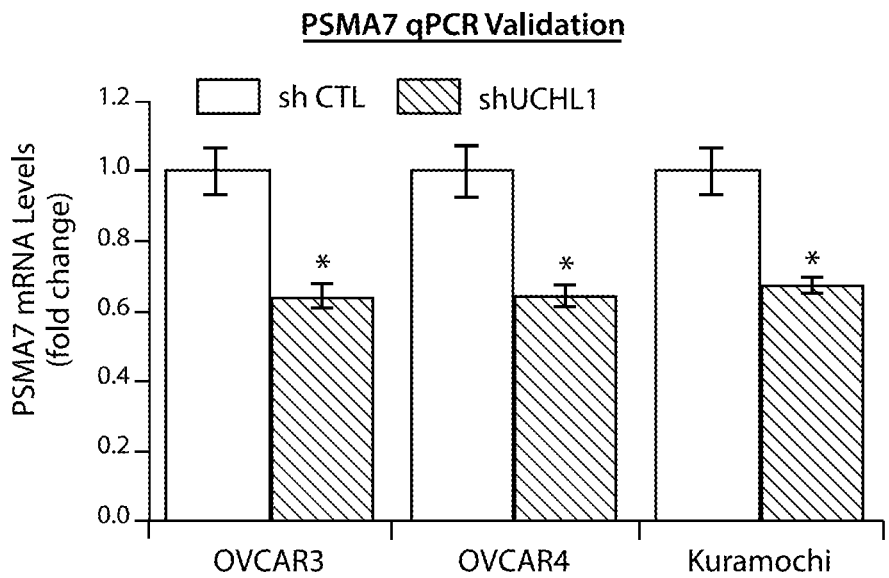

FIG. 12B illustrates QPCR validation of PSMA7 expression in UCHL1 silenced OVCAR3, OVCAR4, and Kuramochi HGSOC cells.

Figure 12C:
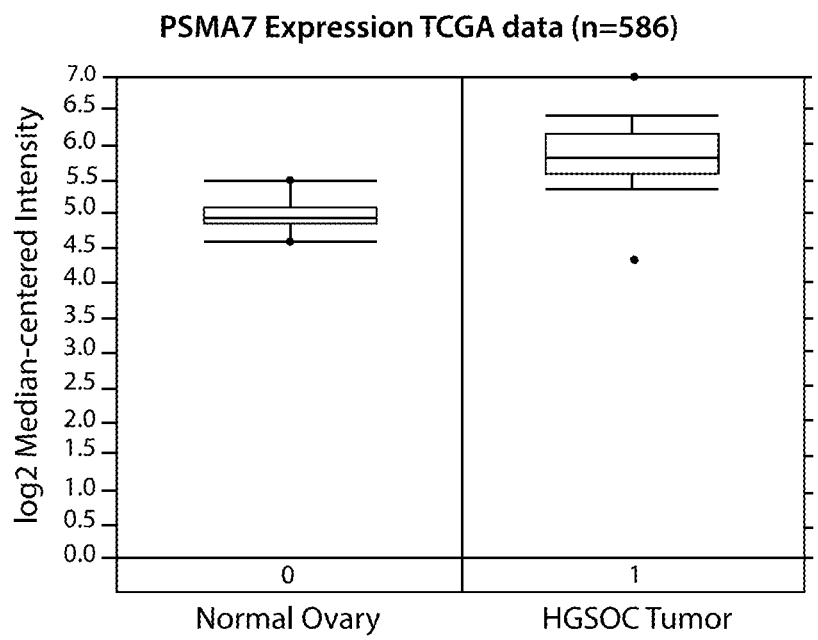

FIG. 12C illustrates increased PSMA7 expression in HGSOC patients primary tumor compared to normal ovary.

Figure 12D:
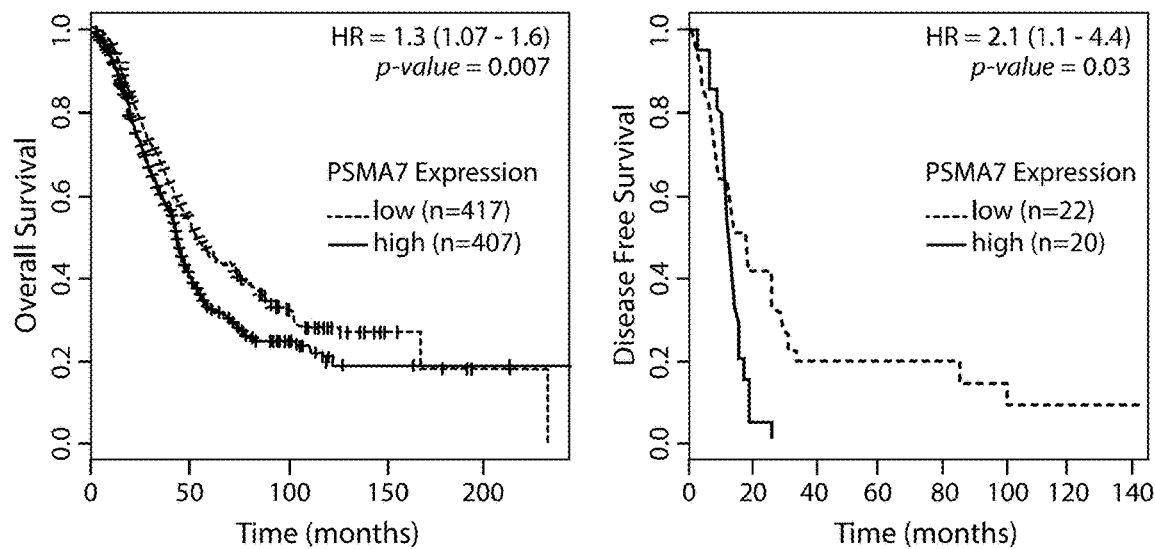

FIG. 12D illustrates survival analysis of HGSOC patients. The analysis demonstrates poor overall survival and progression free survival of patients with elevated PSMA7 levels.

Figure 12E:
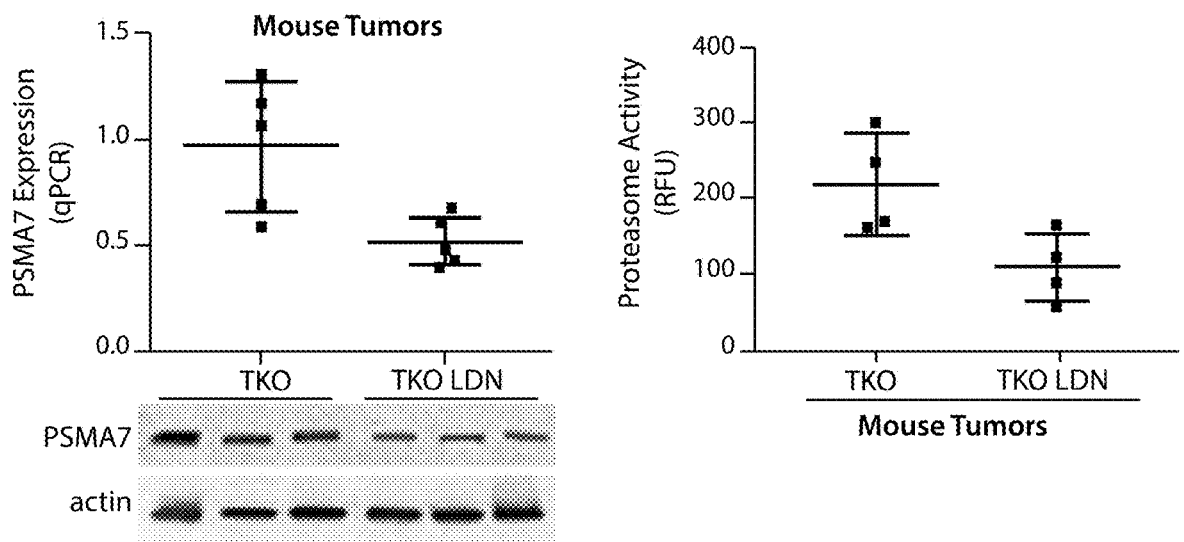

FIG. 12E illustrates analysis of PSMA7 RNA and protein levels in TKO mice.

DESCRIPTION

Where the definition of a term departs from the commonly used meaning of the term, applicant intends to utilize the definitions provided below, unless specifically indicated otherwise.

It is to be understood that the foregoing general description and the following detailed description are exemplary and explanatory only and are not restrictive of any patient matter claimed. In this application, the use of the singular includes the plural unless specifically stated otherwise. It must be noted that, as used in the specification and the appended claims, the singular forms "a," "an" and "the" include plural referents unless the context clearly dictates otherwise.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "comprising", the term "having", the term "including," and variations of these words are intended to be open-ended and mean that there may be additional elements other than the listed elements.

For purposes of the present invention, the term "pharmaceutically acceptable" refers to a compound or drug approved or approvable by a regulatory agency of a federal or a state government, listed or listable in the U.S. Pharmacopeia or in other generally recognized pharmacopeia for use in animals, e.g., mammals, including humans. A "pharmaceutically acceptable carrier" is a carrier which is physiologically acceptable to the patient while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art.

The term "patient" or "patient" as used herein, refers to an animal which is the object of treatment, observation or experiment. By way of example only, a patient may be, but is not limited to, a mammal including, but not limited to, a human.

As will be discussed herein, Applicants have surprisingly discovered the significant oncogenic role of UCHL1 in the context of gain of function p53 mutations using analysis of HGSOC tumor data. Applicants have discovered a dichotomy in expression and function of UCHL1 in wild-type (WT) vs. gain of function p53 mutant conditions.

Without wishing to be bound by any theory, Applicants show that the overexpression of deubiquitinating enzyme, for example UCHL1, in HGSOC mediates transcription-independent function of mutant p53 modulating the cancer cell proteome dynamics via regulating proteasome composition and activity.

The inventors have identified heterogeneity in the expression and function of UCHL1 in ovarian cancer in the context of gain of function p53 mutations. The inventors have demonstrated that UCHL1 overexpression was a common event in HGSOC cell lines harboring different gain of function p53 mutants compared to p53-null or WT p53 OC cell lines. However, in p53-null or wild type p53 conditions, UCHL1 expression was nil or low respectively, which was restored by DNA methylase inhibitor treatment, indicating its down-regulation by hyper-methylation in p53-null or WT p53 conditions. Moreover, UCHL1 was overexpressed in both primary and metastatic HGSOC patient tumors compared to normal adjacent fallopian tube controls and matched primary tumors, respectively. High UCHL1 levels were significantly associated with poor progression free survival of HGSOC patients and low UCHL1 levels were associated with greater median survival (>19 months) of HGSOC patients following chemotherapy compared to those with high UCHL1 ($p=0.001$; GSE9891).

Consistent with this, silencing UCHL1 resulted in significant reduction in HGSOC cell proliferation, migration and invasion. Our RNA-seq data from UCHL1 silenced HGSOC cells revealed a decrease in the expression of proteasomal subunit, alpha 7 (PSMA7), which is associated with proteasomes with increased proteolytic activity and altered composition in oxidative stress. Mass-spectrometry analysis of UCHL1 bound proteins revealed binding of UCHL1 with many proteasomal subunits, including PSMA7, suggesting the role of elevated UCHL1 levels in regulating composition and activity of proteasomes in HGSOC, facilitating mutant p53-mediated degradation of tumor suppressors or cell cycle regulators.

Our analysis of TCGA data showed high expression of PSMA7 in HGSOC patients (median expression log 11.5 fold) and it was associated with poor patient survival. Taken together, our results indicate that UCHL1 overexpression in HGSOC is a key component of mutant p53-mediated oncogenic signaling and results in the deregulation of the proteasome machinery.

In certain aspects the present disclosure provides methods and materials for treatment of cancer. In some forms the present disclosure provides materials and methods for treatment of gynecological, breast, colorectal, pancreatic, and/or lung cancers. In certain embodiments the present disclosure provides methods and materials for treating cervical cancer, gestational trophoblastic disease, primary peritoneal cancer, ovarian cancer, uterine cancer, endometrial cancer, vaginal cancer, uterine carcinosarcoma, and/or vulvar cancers. Any of the methods and/or materials described herein may be used to treat any of the conditions described herein. In certain embodiments the present disclosure provides methods and materials for treatment of cancers associated with over-expression of UCHL1. In certain embodiments the present disclosure provides methods and materials for treatment of cancers associated with a mutated p53 gene. In preferred embodiments the mutated p53 gene is a gain of function p53 mutation. In accordance with certain embodiments the present disclosure provides methods of treating a patient comprising testing for over expression of UCHL1 and/or a p53 mutation, preferably a gain of function p53 mutation.

In some forms the present disclosure provides methods including administering one or more substances to a patient. These materials may comprise a variety of therapeutic substances including but not limited to a: a gene silencing therapeutic, a ubiquitin carboxyl-terminal hydrolase inhibitor, and/or a chemotherapeutic agent. Administration of the therapeutic substance may be performed by any suitable technique known in the art. For example, in some forms one or more therapeutic substances are directly injected into or near a tumor. In some forms, one or more therapeutic substances are delivered systemically, for example intravenously.

In certain embodiments the present disclosure provides a ubiquitin carboxyl-terminal hydrolase inhibitor for use in treating cancer. In some forms such treatments include administration of a ubiquitin carboxyl-terminal hydrolase inhibitor in conjunction with a chemotherapeutic agent. Thus, the present disclosure provides methods for enhancing the effects of chemotherapeutic agents by administering to a patient a pharmaceutically effective amount of a ubiquitin carboxyl-terminal hydrolase inhibitor in conjunction with the administration of the chemotherapeutic agent. Applicants have surprisingly found that silencing or inhibiting UCHL1, for example by silencing p53 and/or MLL2 genes, reduces cancer cell proliferation and migration. Applicants have also found that in certain embodiments inhibiting UCHL1 renders cancers cells more sensitive to chemotherapeutic agents. The chemotherapeutic agent may be any suitable chemotherapeutic agent known in the art, for example: Alkylating Agents, Altretamine, Busulfan, Carboplatin, Carmustine, Chlorambucil, Cisplatin, Cyclophosphamide, Dacarbazine, Lomustine, Melphalan, Oxaliplatin, Temozolomide, Thiotepa, Antimetabolites, 5-fluorouracil (5-FU), 6-mercaptopurine (6-MP), Capecitabine, Cytarabine, Floxuridine, Fludarabine, Gemcitabine, Hydroxyurea, Methotrexate, Pemetrexed, Anti-tumor Antibiotics, Daunorubicin, Doxorubicin, Epirubicin, Idarubicin, Actinomycin-D, Bleomycin, Mitomycin-C, Mitoxantrone, Topoisomerase Inhibitors, Topotecan, Irinotecan (CPT-11), Etoposide (VP-16), Teniposide, Mitotic Inhibitors, Docetaxel, Estramustine, Ixabepilone, Paclitaxel, Vinblastine, Vincristine, Vinorelbine, corticosteroids, Prednisone, Methylprednisolone, Dexamethasone, and/or bortezomib.

Ubiquitin carboxyl-terminal hydrolase inhibitors for use in the presently disclosed methods can be any ubiquitin carboxyl-terminal hydrolase inhibitor suitable for administration to a patient. For example a ubiquitin carboxyl-terminal hydrolase inhibitor may comprise an isatin O-acyl oxime. In certain embodiments the ubiquitin carboxyl-terminal hydrolase inhibitor inhibits ubiquitin carboxyl-terminal hydrolase inhibitor 1. In certain preferred embodiments the ubiquitin carboxyl-terminal hydrolase 1 inhibitor comprises LDN-57444. LDN-57444 is a competitive, reversible, active site-directed inhibitor of UCHL1.

In certain embodiments a pharmaceutically effective amount of LDN-57444 is administered to a patient. In some forms the pharmaceutically effective dose comprises about 0.01 mg to about 100 mg LDN-57444 per kg of patient body weight. In certain preferred embodiments the pharmaceutically effective dose comprises about 0.1 mg to about 10 mg LDN-57444 per kg of patient body weight. In even more preferred embodiments the pharmaceutically effective dose comprises about 0.5 mg to about 5 mg LDN-57444 per kg of patient body weight. In some forms the pharmaceutically effective dose comprises about 1 mg, about 2 mg, about, 3, mg, about 4 mg, and/or about 5 mg LDN-57444 per kg of patient body weight.

As disclosed herein the present disclosure provides for administration of one or more therapeutics effective to silence a target gene. In certain embodiments such gene silencing therapeutics are effective to silence p53 and/or MLL2 genes in a patient. In certain embodiments the gene silencing therapeutic of the present invention provides a temporary effect.

In accordance with certain embodiments, the disclosure provides methods which include testing a patient prior to administration of a therapeutic. In some forms the patient may be tested for overexpression of ubiquitin carboxyl-terminal hydrolase 1, and/or certain genetic mutations. In certain embodiments the patient is tested for mutations in the p53 gene, for example gain-of-function p53 mutations. In certain embodiments a patient is first tested for the presence of a condition, for example over expression of ubiquitin carboxyl-terminal hydrolase 1, and/or genetic mutations, then upon confirmation of the presence of one or more of the conditions the patient may be administered a pharmaceutically effective amount of a ubiquitin carboxyl-terminal hydrolase inhibitor. In certain embodiments a patient may be tested, as described above, concurrent with or following administration of a ubiquitin carboxyl-terminal hydrolase inhibitor. Testing as described herein may be performed by any suitable technique known in the art, for example blood and/or tissue samples may be obtained from the patient. In certain embodiments the patient is known to have cancer and the cancerous tumor is biopsied and tested for over expression of ubiquitin carboxyl-terminal hydrolase 1, and/or p53 mutations.

The following specific Examples are provided to promote a further understanding of certain aspects of the present disclosure. It will be understood that these Examples are illustrative, and not limiting, in character.

EXAMPLE 1

UCHL1 Expression in Various Ovarian Cancer Cell Lines

Figure 1A:
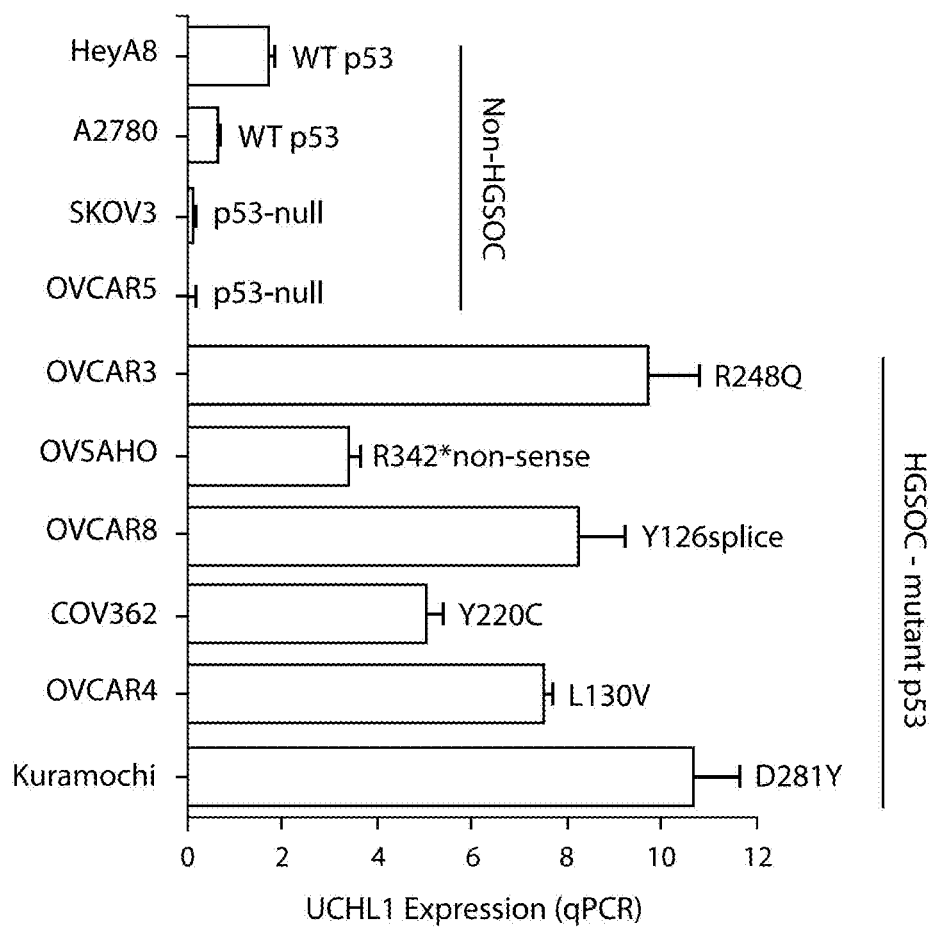
FIG. 1A details results of testing for UCHL1 expression in a panel of HGSOC and non-high-grade serous ovarian cancer cell lines (Non-HRSOC).
Figure 1A:
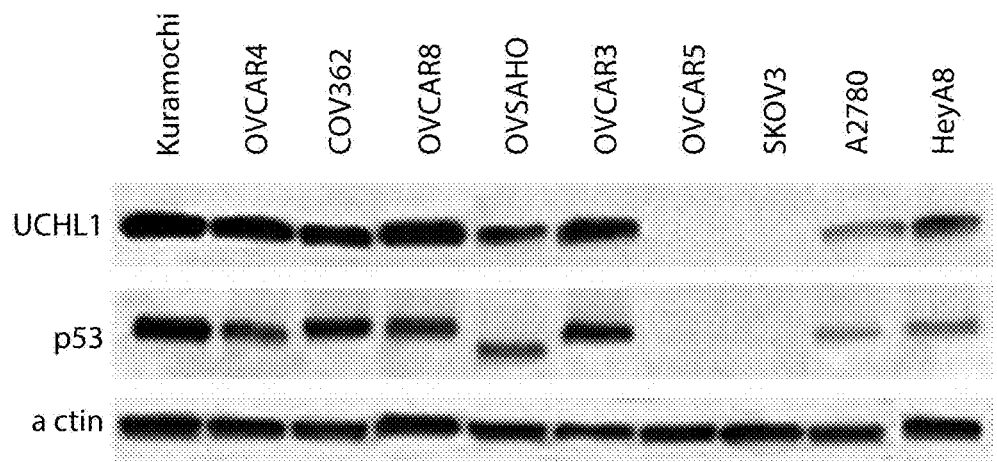

FIG. 1A details results of testing for UCHL1 expression in a panel of HGSOC (mutant p-53) and non-high-grade serous ovarian cancer cell lines (Non-HGSOC). Each of the HGSOC cell lines had identified gain of function p53 mutations. The Non-HGSOC cell lines were either wild type (WT) or included p53 null mutations. UCHL1 expression was significantly increased in HGSOC ovarian cancer cell lines carrying different p53 mutations. However in p53 null or wild type p53 conditions UCHL1 expression was absent or low respectively.

Figure 1B:
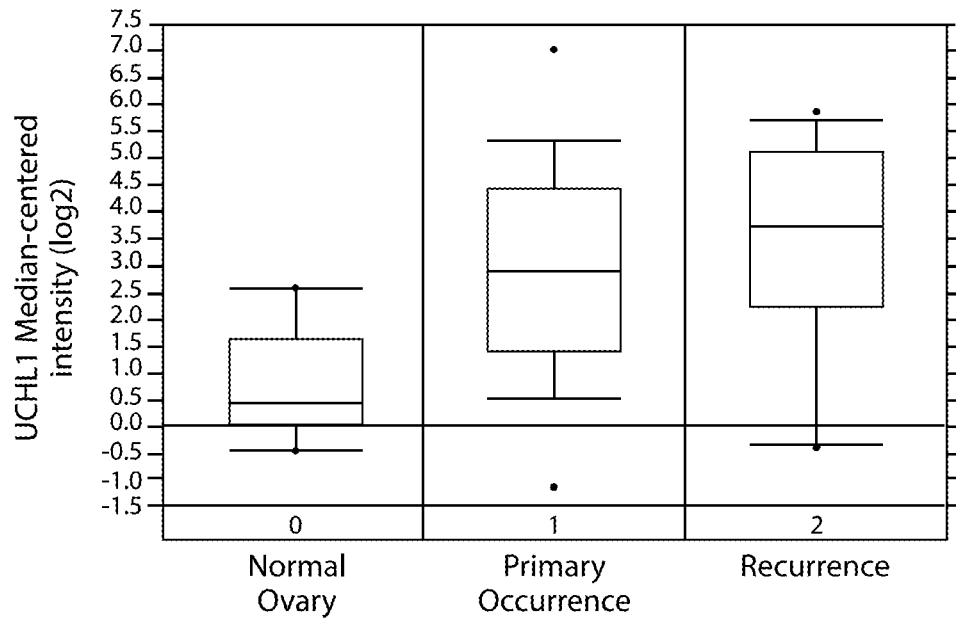
FIG. 1B details elevated UCHL1 expression in HGSOC patients' primary tumors and recurrent tumors compared to normal ovarian tissue.

FIG. 1B details elevated UCHL1 levels in HGSOC patients' primary tumors and recurrent tumors compared to normal ovarian tissue.

Figure 1C:
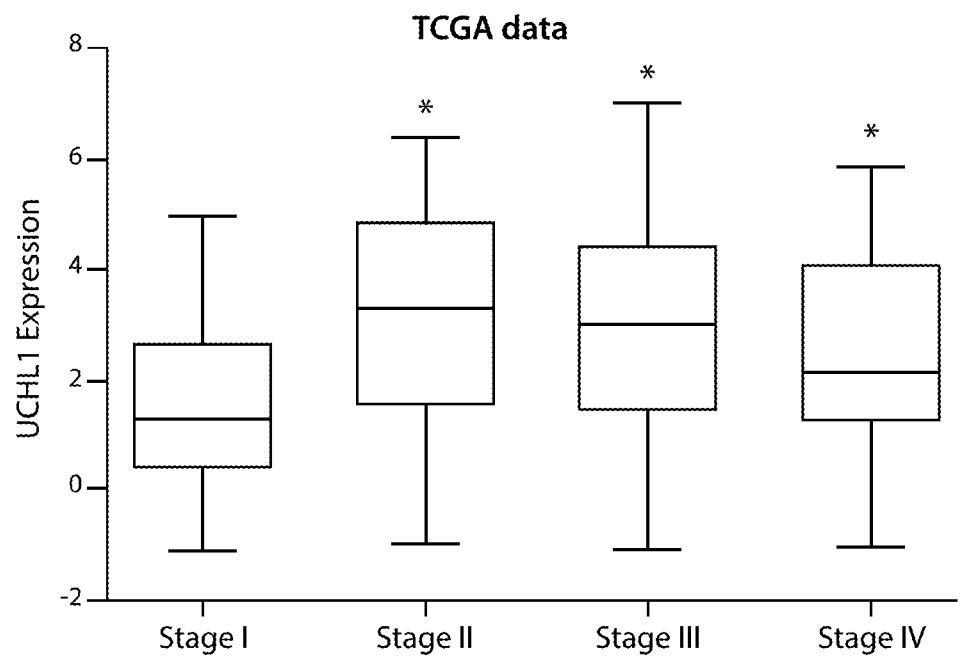
FIG. 1C details elevated UCHL1 levels in more advanced stage II, stage III, and stage IV tumors of HGSOC patients compared to stage I.

FIG. 1C details elevated UCHL1 levels in more advanced stage II (n=27), stage III (n=436), and stage IV (n=84) tumors of HGSOC patients compared to stage I (n=16).

Figure 1D:
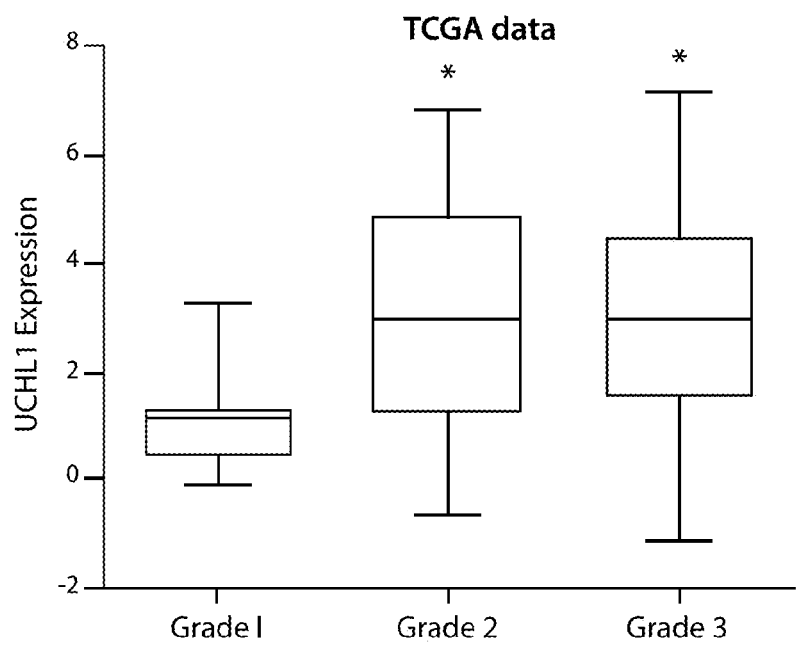
FIG. 1D details elevated UCHL1 levels in more aggressive grade 2 and grade 3 tumors of HGSOC patients compared to grade 1 tumors.

FIG. 1D details elevated UCHL1 levels in more aggressive grade 2 (n=69) and grade 3 (n=479) tumors of HGSOC patients compared to grade 1 (n=6) tumors.

EXAMPLE 2

UCHL1 Expression Across Gynecological Cancers

Figure 2:
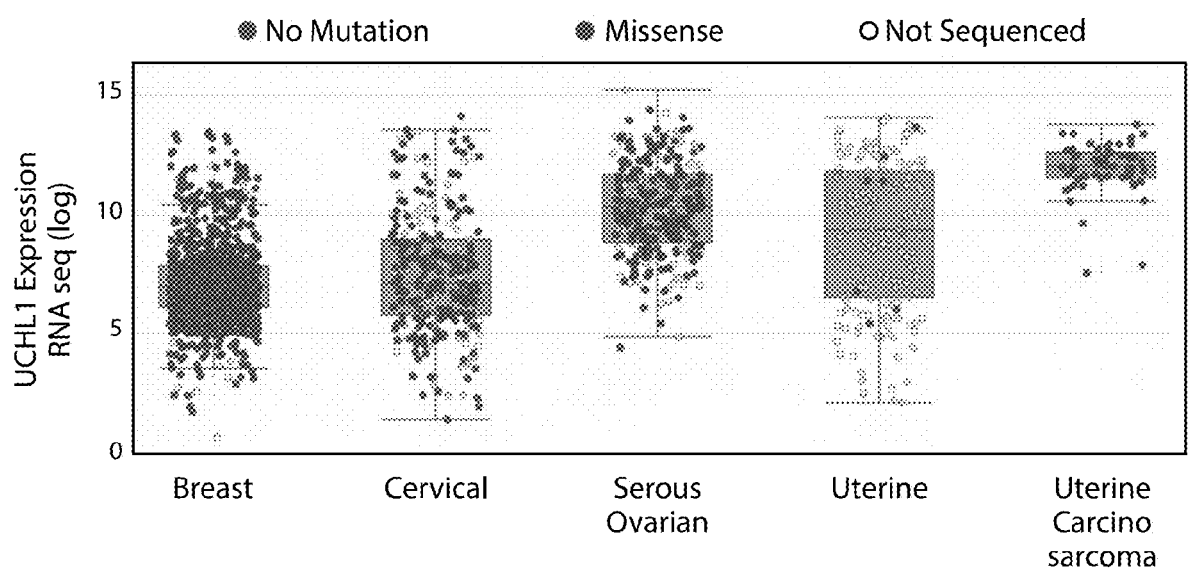
FIG. 2 details results of a cBioportal analysis of TCGA (The Cancer Genome Atlas) databases for UCHL1 expression in breast cancer, cervical cancer, serous ovarian cancer, uterine cancer, and uterine carcinosarcoma.

FIG. 2 details results of a cBioportal analysis of TCGA (The Cancer Genome Atlas) databases for UCHL1 expression in breast cancer, cervical cancer, serous ovarian cancer, uterine cancer, and uterine carcinosarcoma. These results show that UCHL1 is expressed at higher average rates in Serous Ovarian cancers, Uterine Carcinosarcomas, and some uterine cancers.

EXAMPLE 3

UCHL1 Expression in HGSOC Patient Tumors v. Normal Adjacent Tissue

Figure 3:
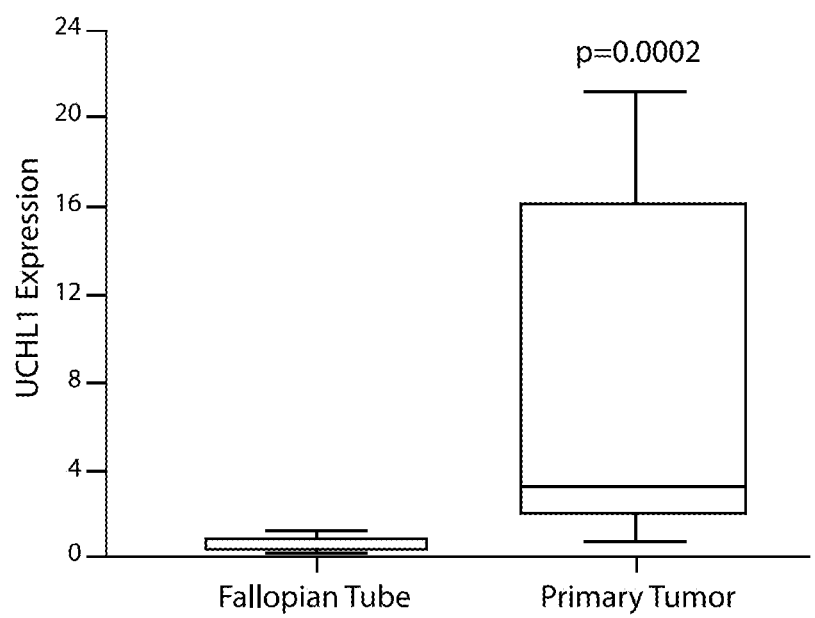
FIG. 3 details expression levels of UCHL1 in primary tumor HGSOC tissue and expression levels of UCHL1 in paired adjacent normal fallopian tube tissue.
Figure 4:
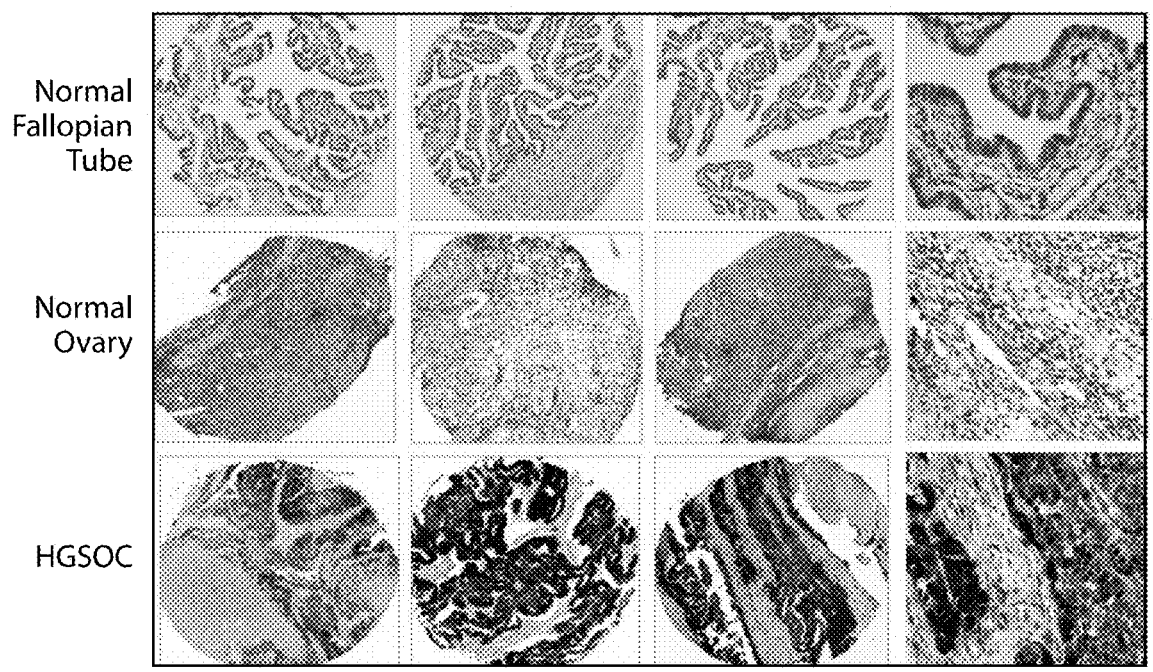
FIG. 4 shows IHC staining images of UCHL1 in tissue microarray (TMA) of HGSOC patients and normal fallopian tube and ovary tissue.
Figure 5A:
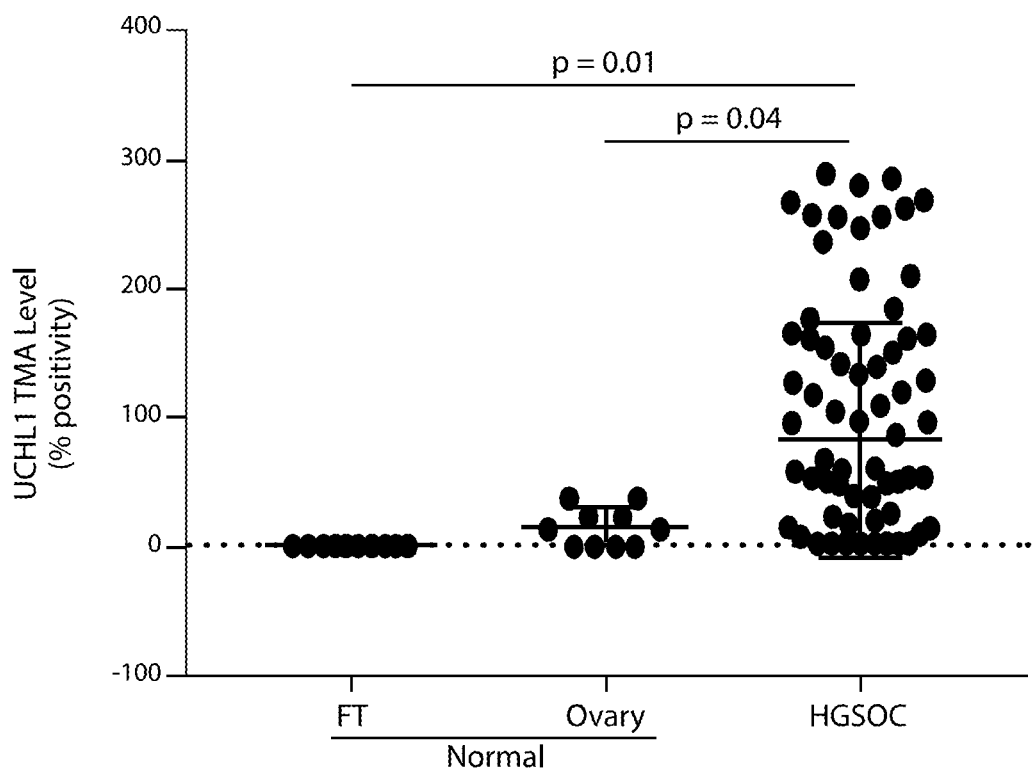
FIG. 5A illustrates a quantitative analysis of TMA revealing significant overexpression of UCHL1 in HGSOC patients.
Figure 5B:
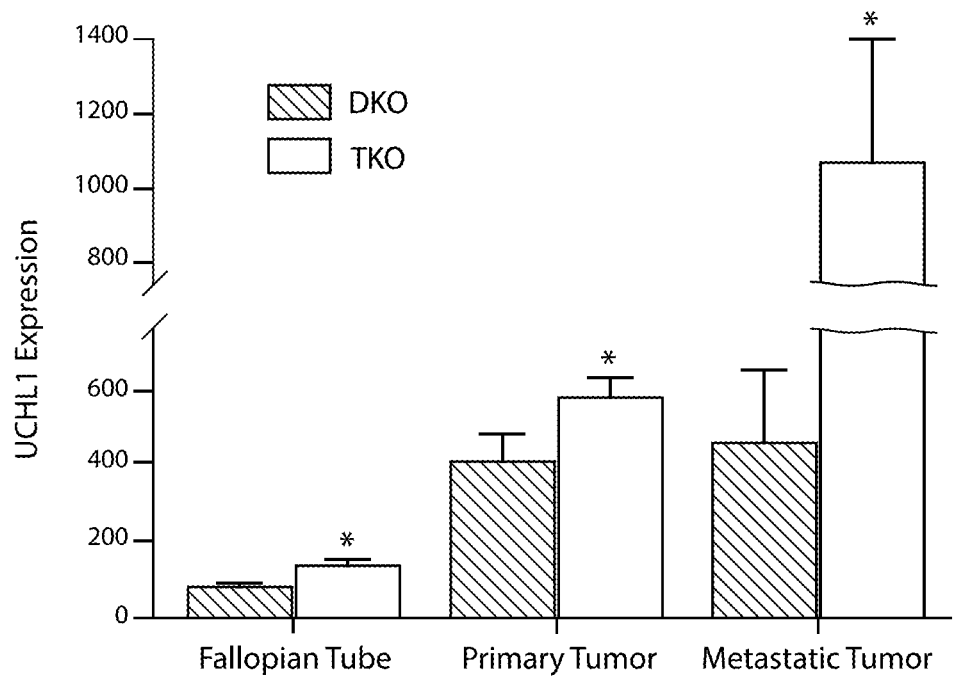
FIG. 5B illustrates UCHL1 levels in fallopian tube tissue, primary tumor tissue, and metastatic tumor tissue (RNA-seq) in triple mutant (TKO) (Pten−/− Dicer−/− and p53-R172H) and Double Knock out (DKO) (Pten−/− Dicer−/−) HGSOC mouse models.
Figure 5C:
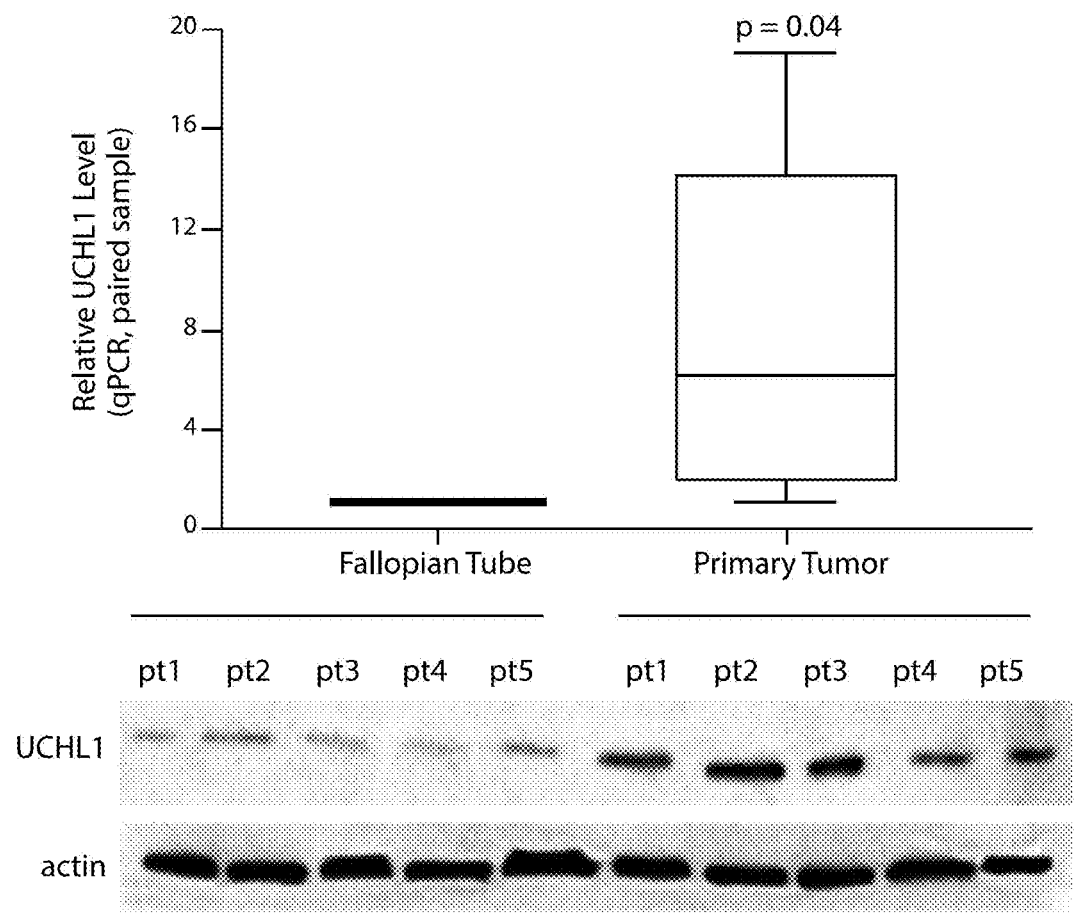
FIG. 5C illustrates UCHL1 expression levels in primary tumor HGSOC tissue and expression levels of UCHL1 in pared (from the same patient) adjacent normal fallopian tissue.
Figure 5D:
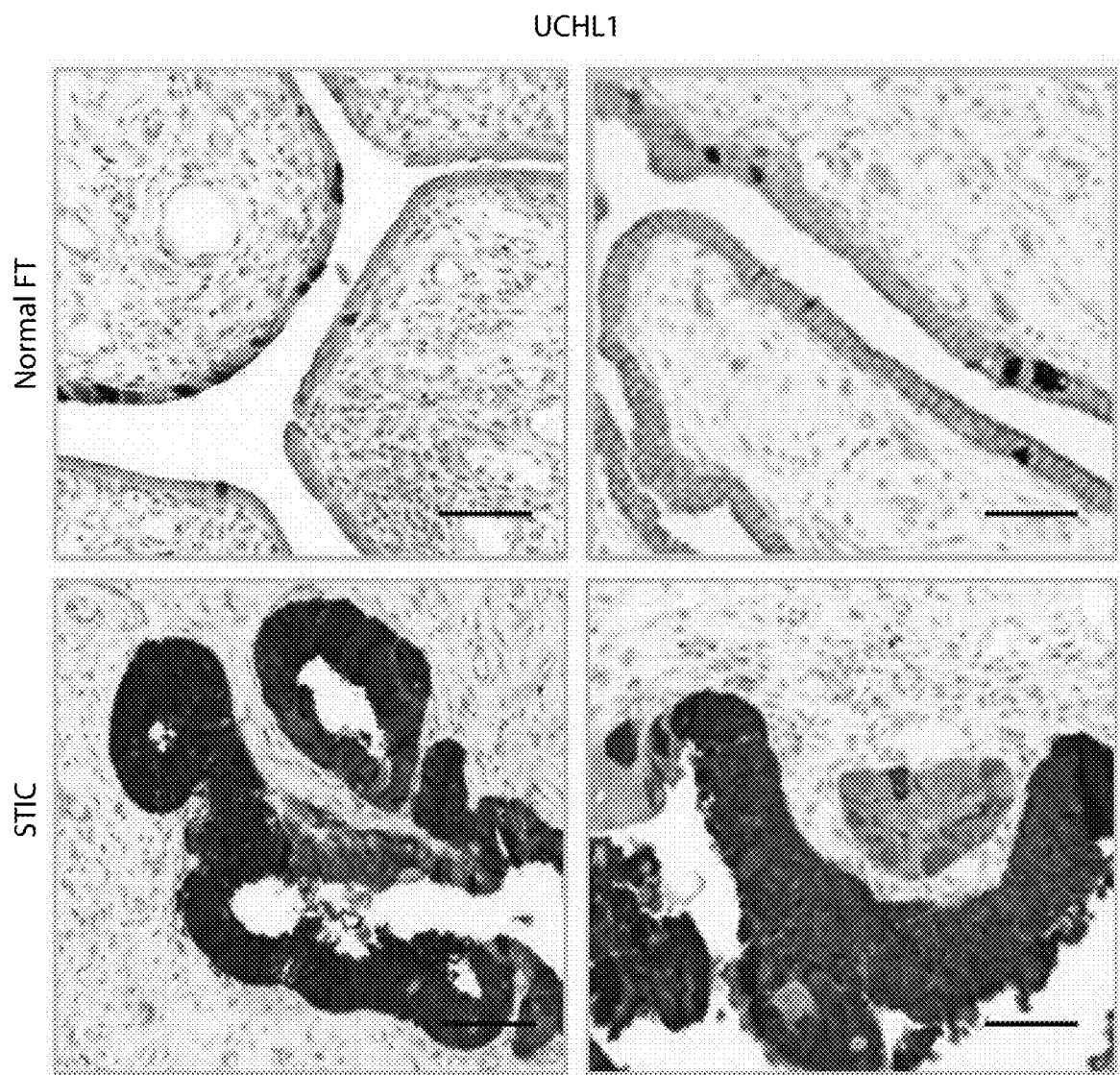
FIG. 5D includes IHC staining images in normal human fallopian tube and fallopian tube with precursor lesion of HGSOC—called STIC (Serous Tubal Intraepithelial Cancer).

Strong UCHL1 expression was observed in 66% of HGSOC patients (44 out of 67 tumors in a tissue microarray). FIG. 3 details expression levels of UCHL1 in primary tumor HGSOC tissue and expression levels of UCHL1 in paired adjacent normal fallopian tube tissue. Expression of UCHL1 was elevated in primary tumors from patients with HGSOC compared to the matched normal fallopian tubes. FIG. 4 shows IHC staining images of UCHL1 in tissue microarray (TMA) of HGSOC patients and normal fallopian tube and ovary tissue. FIG. 5A illustrates a quantitative analysis of TMA reveling significant overexpression of UCHL1 in HGSOC patients over normal (Non-cancerous) fallopian tube (FT) and ovary tissues. FIG. 5B illustrates UCHL1 levels in fallopian tube tissue, primary tumor tissue, and metastatic tumor tissue (RNA-seq) in triple mutant (TKO) (Pten-/- Dicer-/- and p53-R172H) and Double Knock out (DKO) (Pten-/- Dicer-/-) HGSOC mouse model. FIG. 5C illustrates UCHL1 expression levels in primary tumor HGSOC tissue and expression levels of UCHL1 in pared (from the same patient) adjacent normal fallopian tissue. FIG. 5D includes IHC staining images in normal human fallopian tube and fallopian tube with precursor lesion of HGSOC—called STIC (Serous Tubal Intraepithelial Cancer). These results indicate that UCHL1 is overexpressed in certain cancers.

EXAMPLE 4

UCHL1 Levels and Survival

Figure 6A:
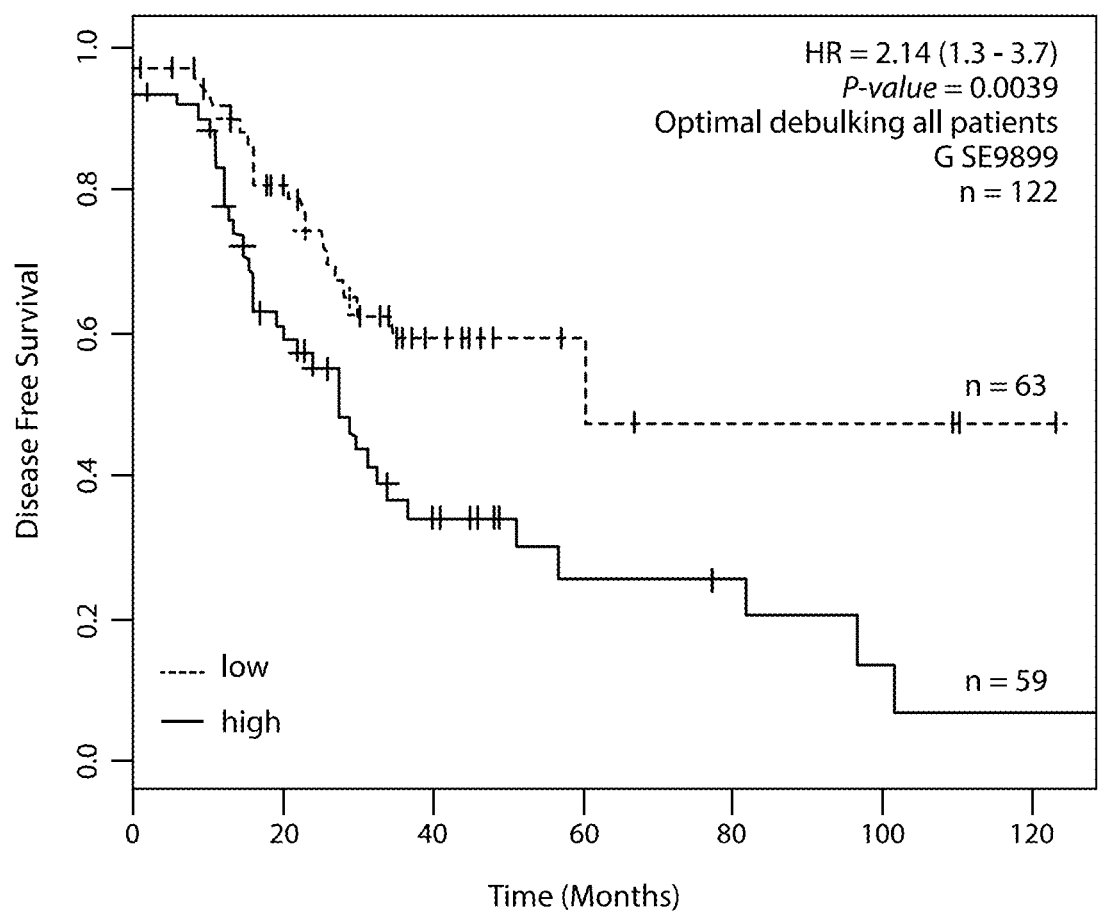
FIGS. 6A-C depicts Kaplan Meier survival curves of HGSOC patients demonstrating the effect of UCHL1 expression on A) disease free survival, B) progression free survival and C) overall survival of HGSOC patients, respectively, after chemotherapy.
Figure 6B:
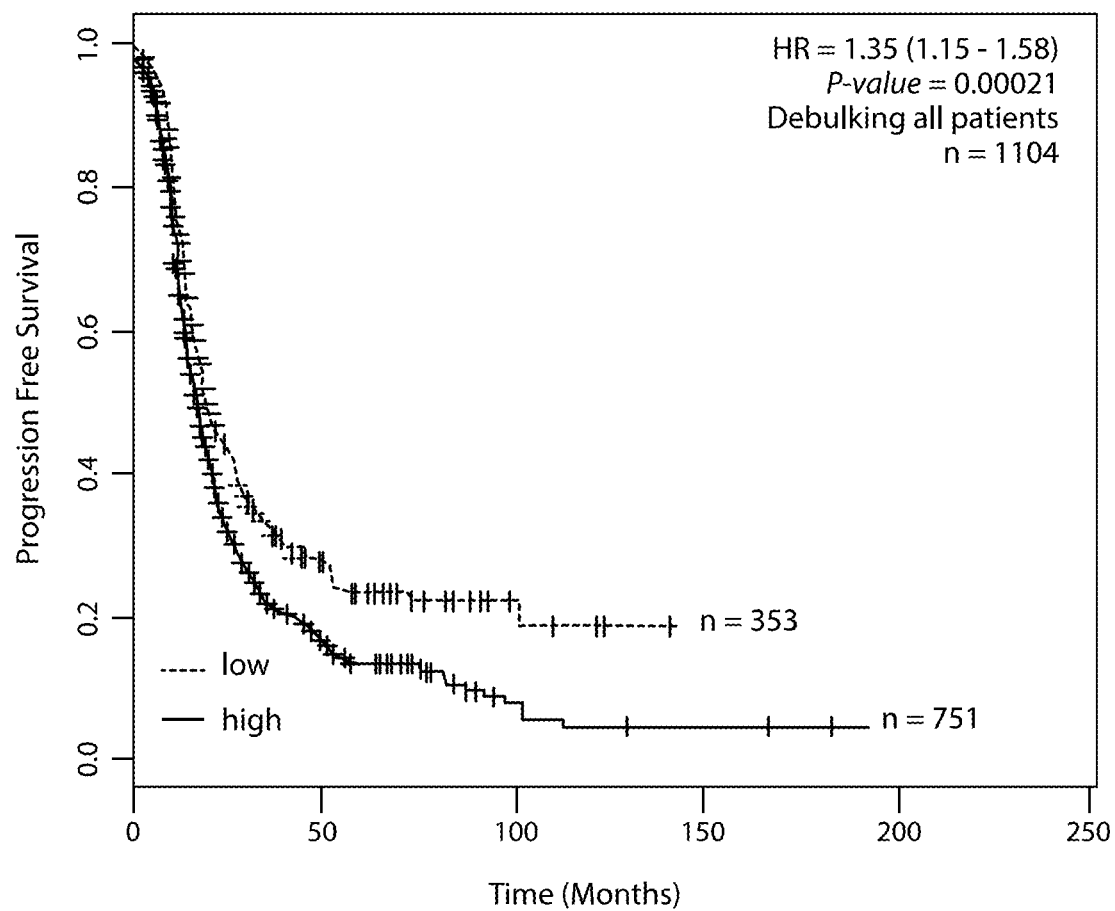
Figure 6C:
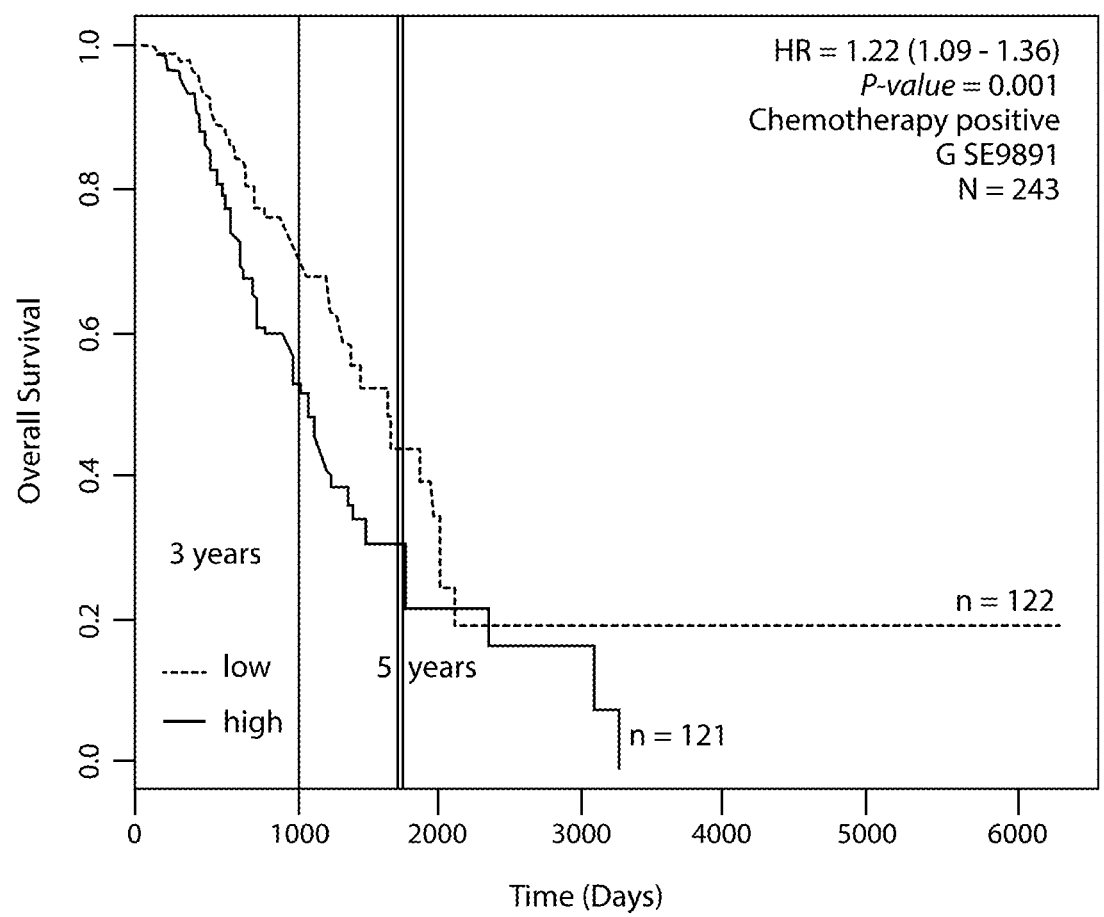

FIGS. 6A-C depict Kaplan Meier survival curves of HGSOC patients demonstrating the effect of UCHL1 expression on A) disease free survival, B) progression free survival, and C) overall survival of HGSOC patients after chemotherapy. FIG. 6A is a Kaplan-Meier plot showing poor disease-free survival of HGSOC patients with elevated UCHL1 levels. Patent data for this analysis was from Molecular Therapeutics for Cancer, Ireland (MTCI) and GSE9899. FIG. 6B illustrates high UCHL1 levels were associated with poor progression free survival. FIG. 6C illustrates that the overall survival of HGSOC patients given chemotherapy was poor in patients with elevated levels of UCHL1. Post chemotherapy low UCHL1 levels were associated with greater (>19 months) median survival of HGSOC patients vs. high UCHL1 levels (p=0.001; GSE9891). Similarly, HGSOC patients were classified into high or low UCHL1 expressing groups based on UCHL1 median expression. The p-value from log-rank tests comparing two KM curves is shown for each. These results indicate that higher expression levels of UCHL1 is correlated with poor patient progression free survival.

EXAMPLE 5

UCHL1 Expression

Figure 7A:
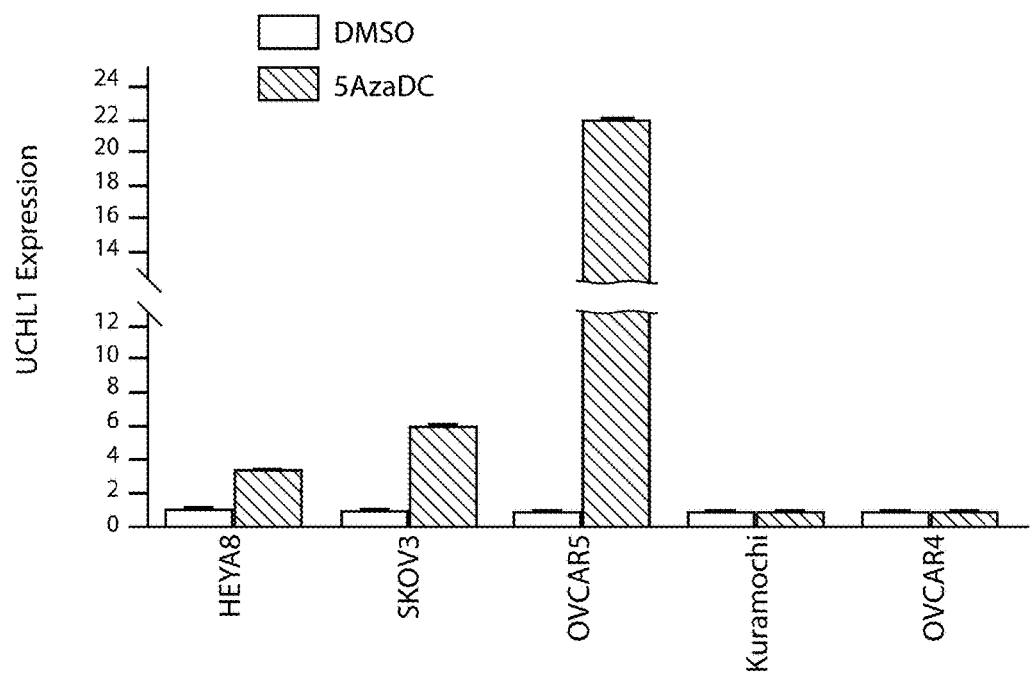
FIG. 7A depicts relative UCHL1 expression (qPCR) after treatment with DNA methylase inhibitor, 5AzaDC (200 μM, day 3) in ovarian cancer cells.

FIG. 7A depicts relative UCHL1 expression (qPCR) after treatment with DNA methylase inhibitor, 5AzaDC (200 µM, day3) in ovarian cancer cells. The following cell cultures were included in the analysis: HeyA8 (WT p53), SKOV3 (p53 null), OVCAR5 (p53 null), Kuramochi (mutant p53), and OVCAR4 (mutant p53).

Figure 7B:
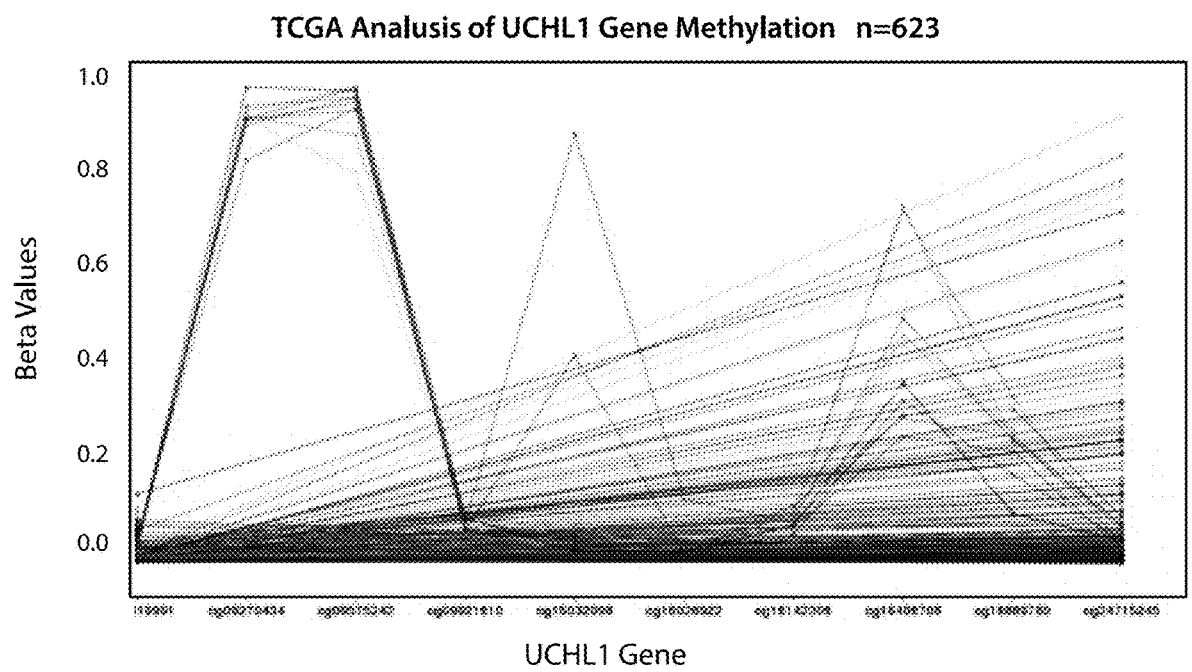
FIG. 7B depicts beta values of UCHL1 gene determined by analysis of 450K methylation array in the TCGA database of HGSOC patients. Beta value zero means no methylation.

FIG. 7B depicts beta values of UCHL1 gene determined by analysis of 450K methylation array in TCGA database of HGSOC patients. Beta value zero means no methylation.

Figure 7C:
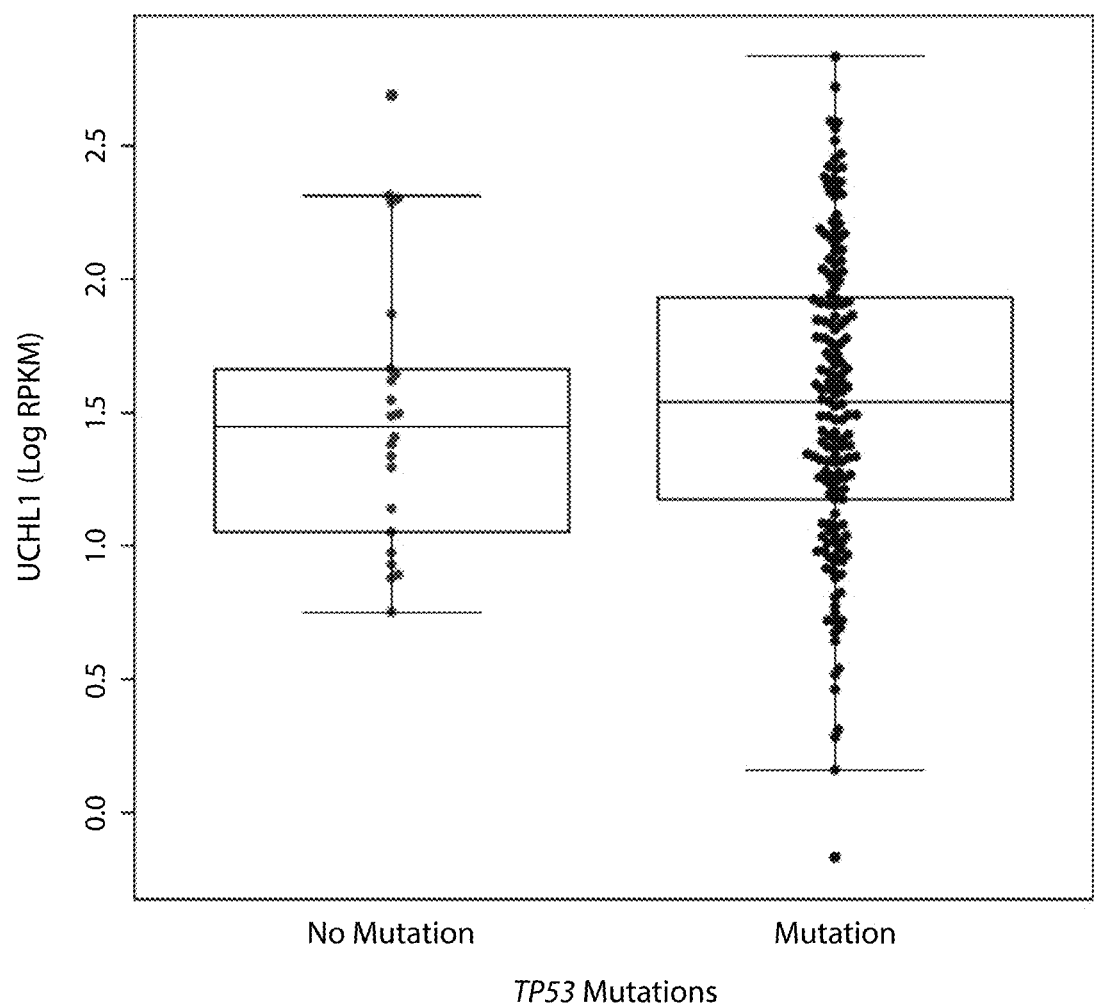
FIG. 7C depicts UCHL1 expression in ovarian cancer patients with or without mutation in p53 gene in the TCGA database, analyzed using firebrowse.

FIG. 7C depicts UCHL1 expression in ovarian cancer patients with or without mutation in p53 gene in TCGA database, analyzed using firebrowse.

Figure 7D:
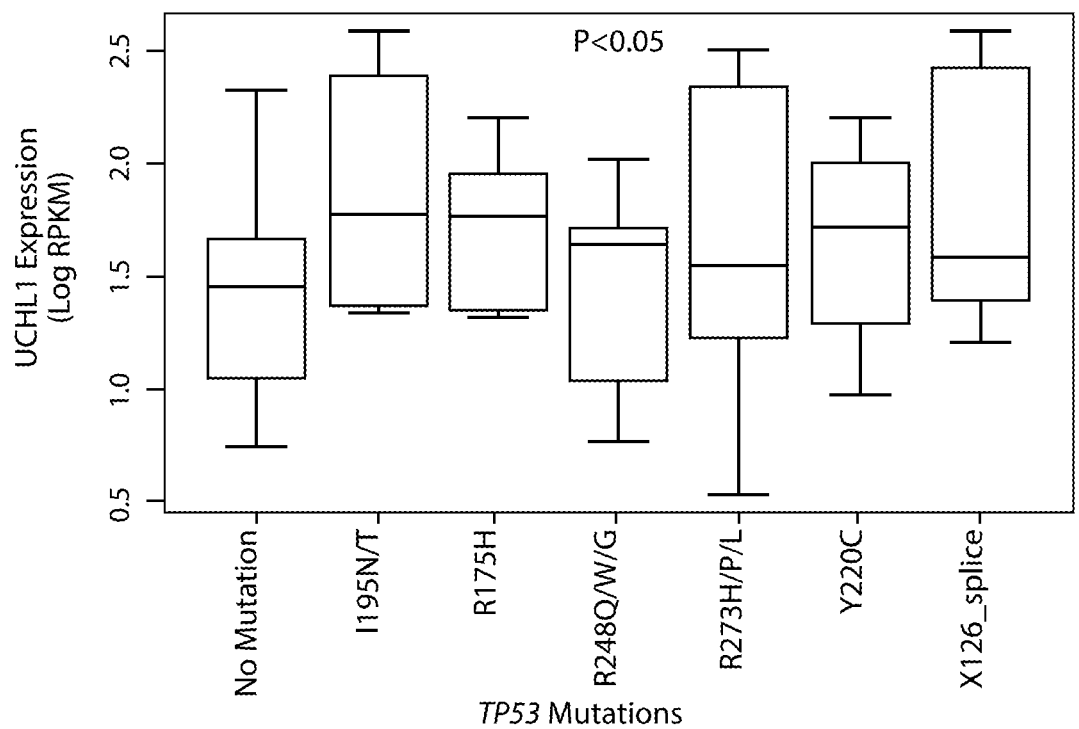
FIG. 7D depicts UCHL1 expression in HGSOC patients with different gain-of-function p53 mutations.

FIG. 7D depicts UCHL1 expression in HGSOC patients with different gain-of-function p53 mutations (TCGA database, firebrowse, RPKM: reads per kilobase of transcript per million mapped).

Figure 7E:
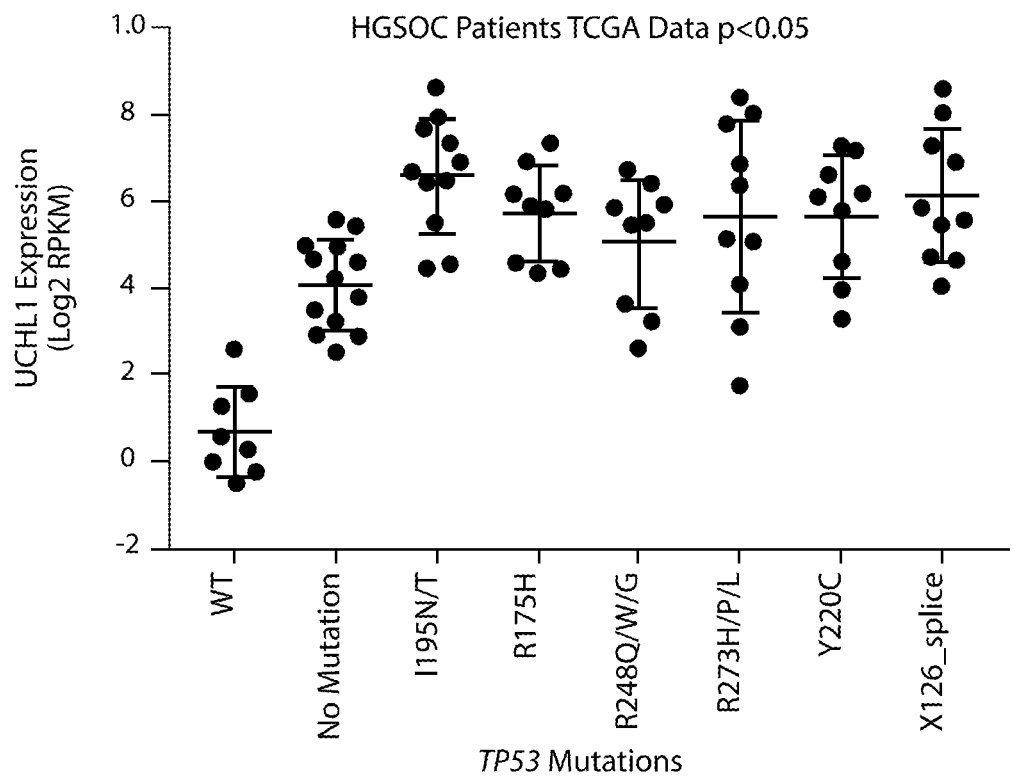
FIG. 7E depicts differential high expression of UCHL1 in HGSOC patients with different TP53 mutations compared to patients with wild type and no mutations.

FIG. 7E depicts differential high expression of UCHL1 in HGSOC patients with different TP53 mutations compared to patients with wild type (WT p53) and no mutations.

Figure 7F:
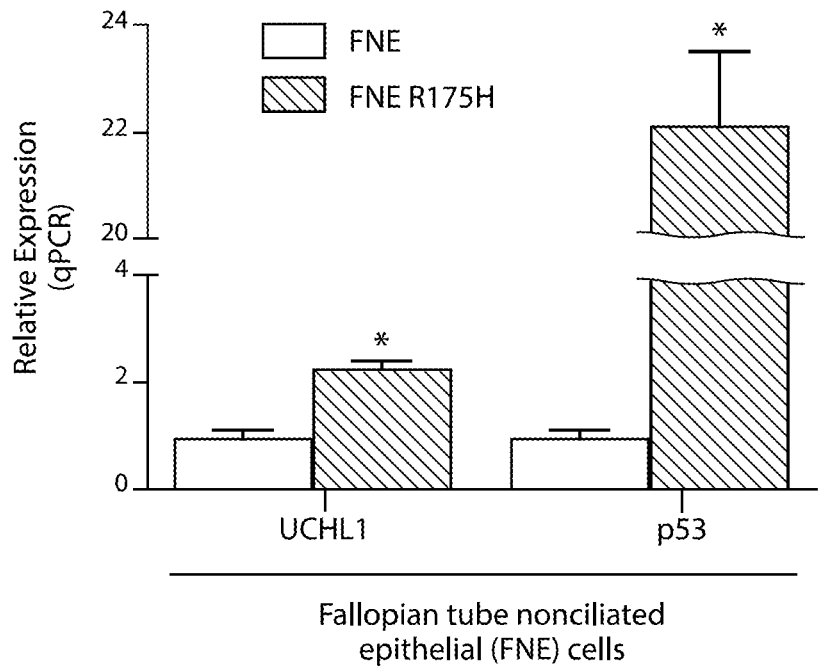
FIG. 7F depicts overexpression of mutant p53 variant R175H in normal human fallopian tube epithelial cells resulted in high UCHL1 expression.

FIG. 7F depicts overexpression of mutant p53 variant R175H in normal human fallopian tube epithelial cells resulted in high UCHL1 expression.

Figure 7G:
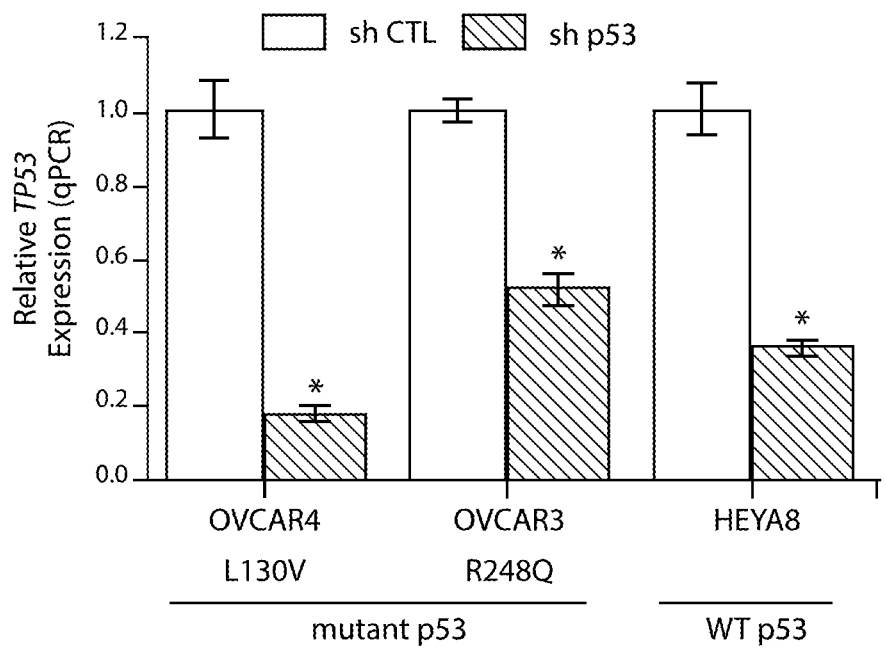
FIG. 7G depicts the results of silencing TP53 in HGSOC cell lines OVCAR3 and OVCAR4 with mutant TP53 variants R248Q and L130V respectively resulted in reduction of UCHL1 levels. TP53 silencing in WT p53 cell line HeyA8 had no significant effect on UCHL1 levels.

FIG. 7G depicts the results of silencing TP53 in HGSOC cell lines OVCAR3 and OVCAR4 with mutant TP53 variants R248Q and L130V respectively resulted in reduction of UCHL1 levels. TP53 silencing in WT p53 cell line HeyA8 had no significant effect on UCHL1 levels.

Figure 7H:
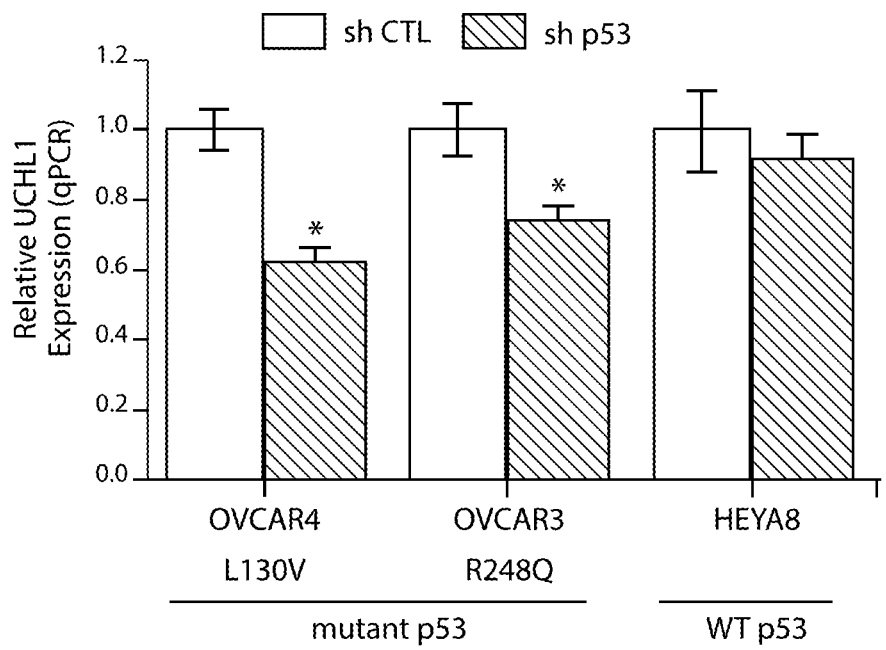
FIG. 7H depicts relative UCHL1 expression (qPCR) after treatment with DNA methylase inhibitor, 5AzaDC in ovarian cancer cells with wild-type p53, ovarian cancer cells with p53-null mutations and normal fallopian tube cells with wild-type p53.
Figure 7H:
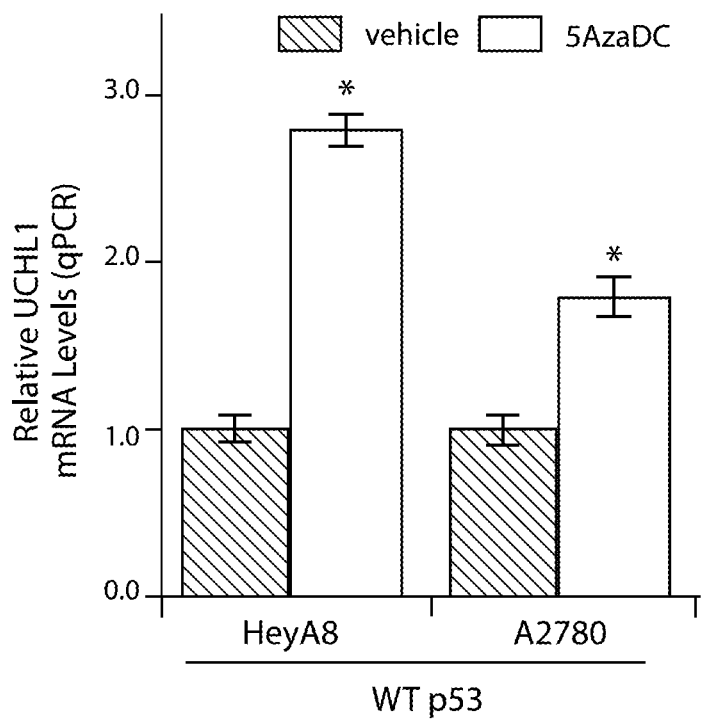

FIG. 7H depicts relative UCHL1 expression (qPCR) after treatment with DNA methylase inhibitor, 5AzaDC (200 µM, day 2) in ovarian cancer cells with wild-type p53 (HeyA8 and A2780), ovarian cancer cells with p53-null mutations (OVCAR5 and SKOV3) and normal fallopian tube cells with wild-type p53 (FTE282).

Figure 7I:
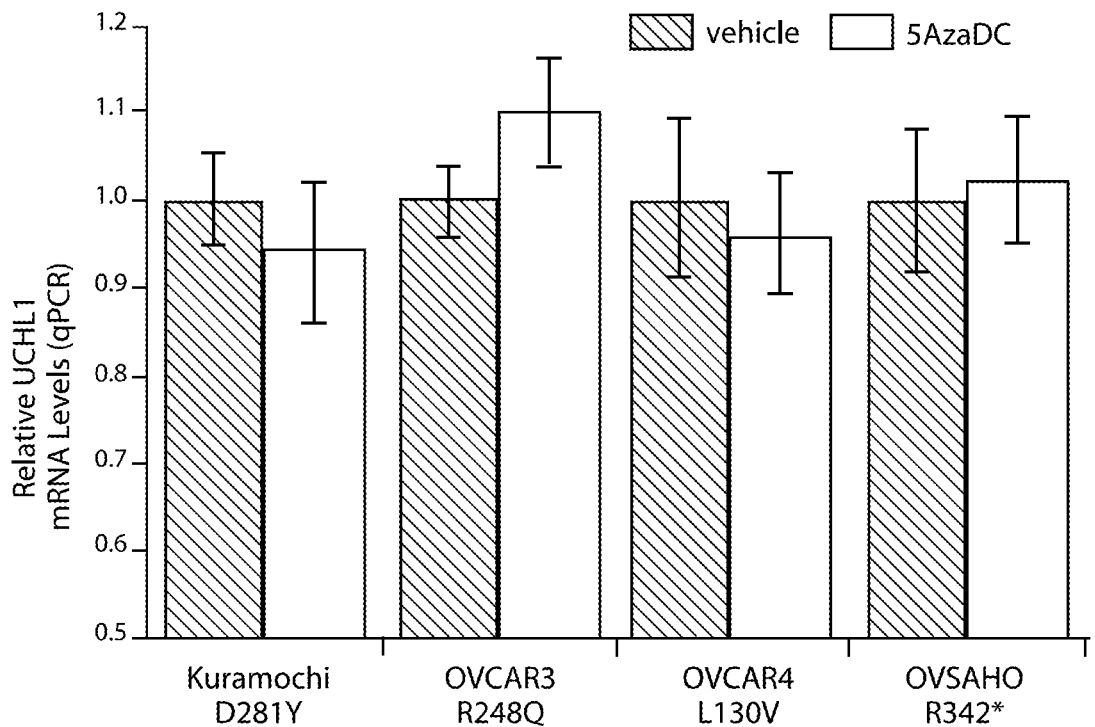
FIG. 7I illustrates that no change in UCHL1 levels were detected with treatment with DNA methylase inhibitor 5AzaDC in HGSOC cell lines with mutant p53.

FIG. 7I illustrates that no change in UCHL1 levels were detected with treatment with DNA methylase inhibitor 5AzaDC (200 µM, day 2) in HGSOC cell lines with mutant p53.

Figure 7J:
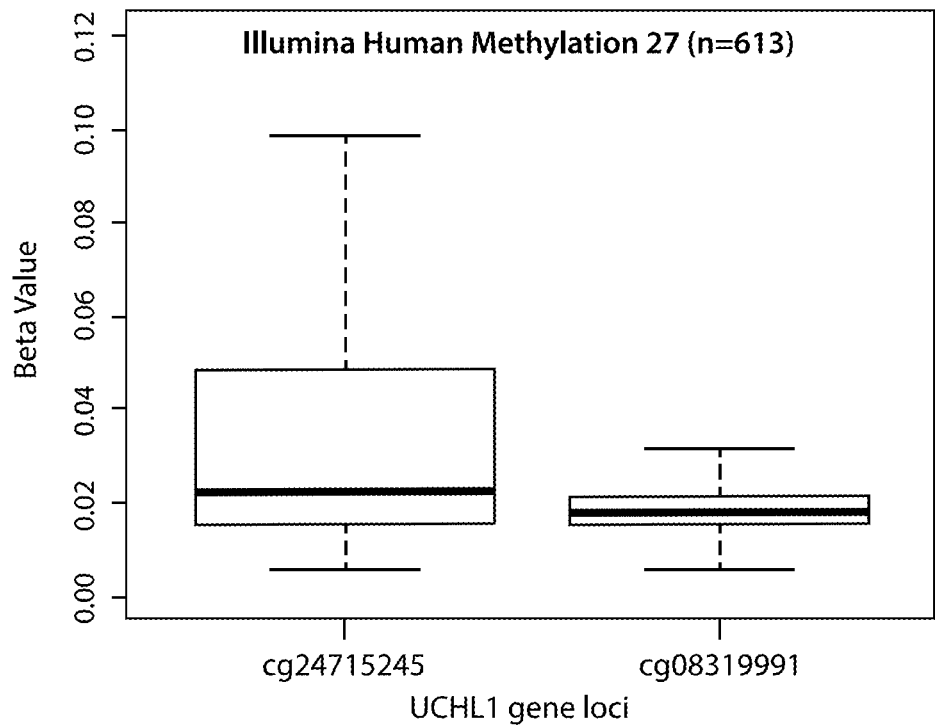
FIG. 7J depicts the results of an analysis of UCHL1 gene methylation.

FIG. 7J depicts the results of an analysis of UCHL1 gene methylation using Illumina Human Methylation 27 data of HGSOC patients from GDC (Genomic Data Commons of National Cancer Institute) TCGA (The Cancer Genome Atlas) ovarian cancer database and UCSC (University of California Santa Cruz) Xena browser. Beta value 0 means no methylation while beta value 1 means complete methylation. This data reflects the ratio of intensities between methylated and unmethylated alleles.

FIG. 7K depicts results of TP53 silencing in reducing expression of histone methyltransferase MLL2 in OVCAR3 and OVCAR4 cells with mutant R248Q and L130V p53 mutants respectively. ChIP-qPCR was also performed showing mutant p53 enrichment on MLL2 promoter in OVCAR3 cells.

Figure 7L:
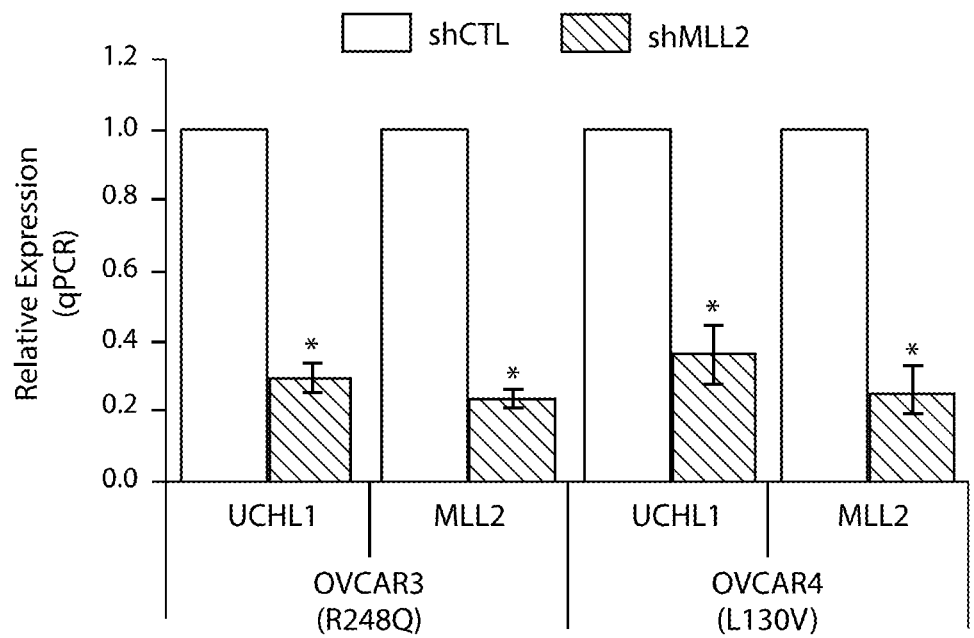
FIG. 7L depicts results of an experiment silencing MLL2 in OVCAR 3 and OVCAR4 cells.

FIG. 7L depicts results of an experiment silencing MLL2 in OVCAR 3 and OVCAR4 cells. This resulted in reduced UCHL1 expression in HGSOC cells. This result illustrates the role of mutant p53 and MLL2 in UCHL1 overexpression in HGSOC.

EXAMPLE 6

Cellular Activity of UCHL1 Silenced Cell Lines

Silencing UCHL1 exhibited significant reduction in HGSOC proliferation, migration, and invasion. UCHL1 expression was silenced using siUCHL1 (UCHL1 silencing RNA) and shUCHL1 (UCHL1 short hairpin RNA) in mutant p53 expressing HGSOC cells. The cell lines used for this experiment include: Kuramochi (D281Y), OVCAR3 (R248Q), OVSAHO (R342* non-sense), and OVCAR4

Figure 8A:
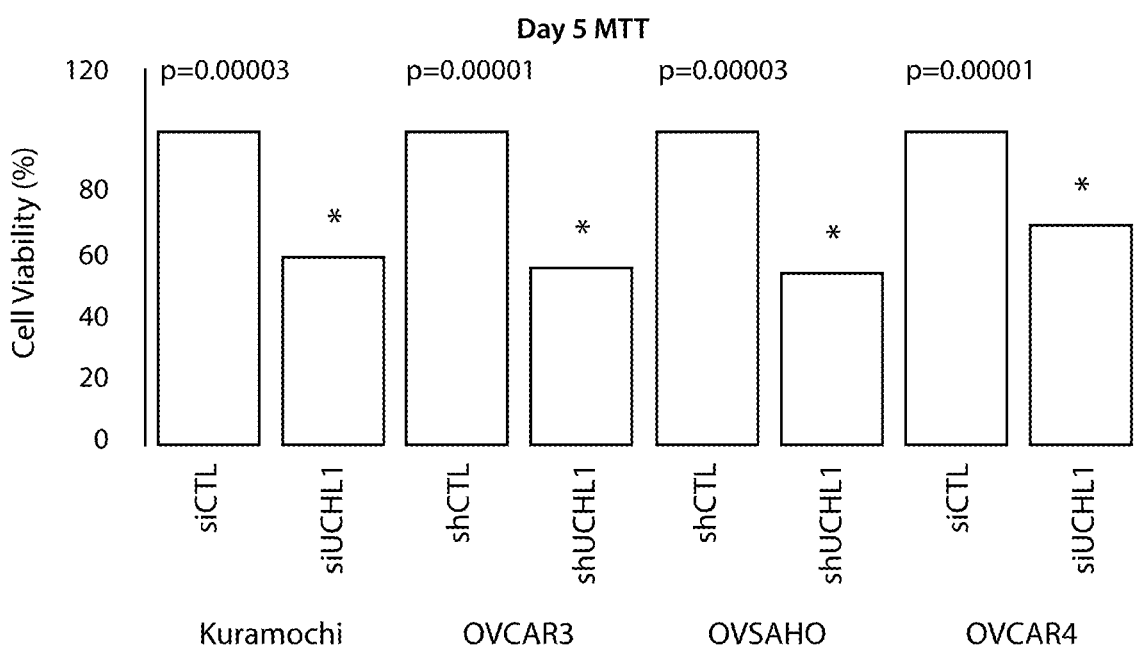
FIG. 8A depicts a significant reduction in cellular proliferation (5-day) of UCHL1 silenced cells.

(L130V). The UCHL1 silenced cells exhibited a significant reduction in cellular proliferation (5-day) as depicted in FIG. 8A.

Figure 8B:
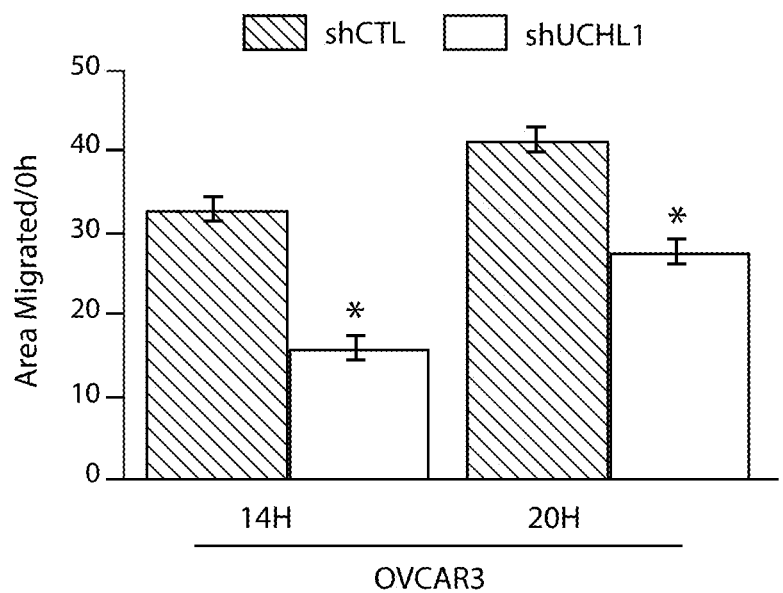
FIG. 8B depicts a significant decrease in migration of UCHL1 silenced OVCAR3 cells compared to unsilenced controls. The wound healing assay was performed using a 2 well silicon insert.
Figure 8B:
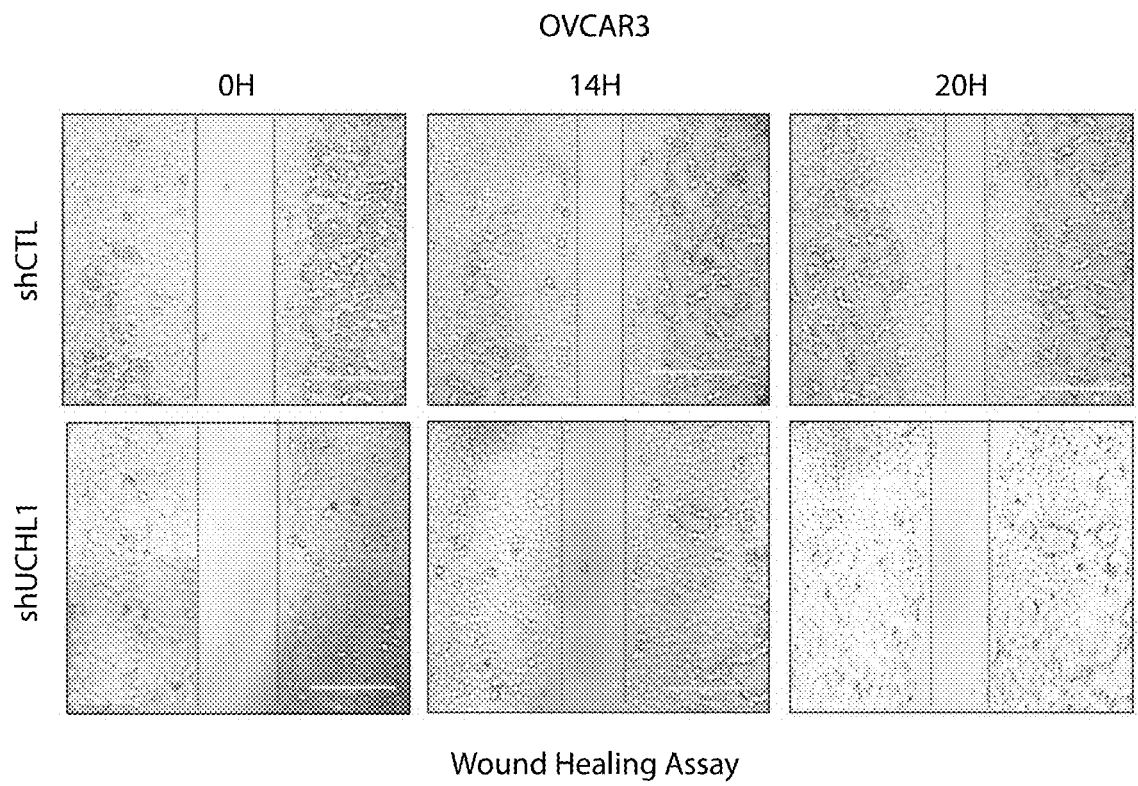

FIG. 8B depicts a significant decrease in migration of UCHL1 silenced OVCAR3 cells compared to unsilenced controls. The wound healing assay was performed using a 2 well silicon insert.

Figure 8C:
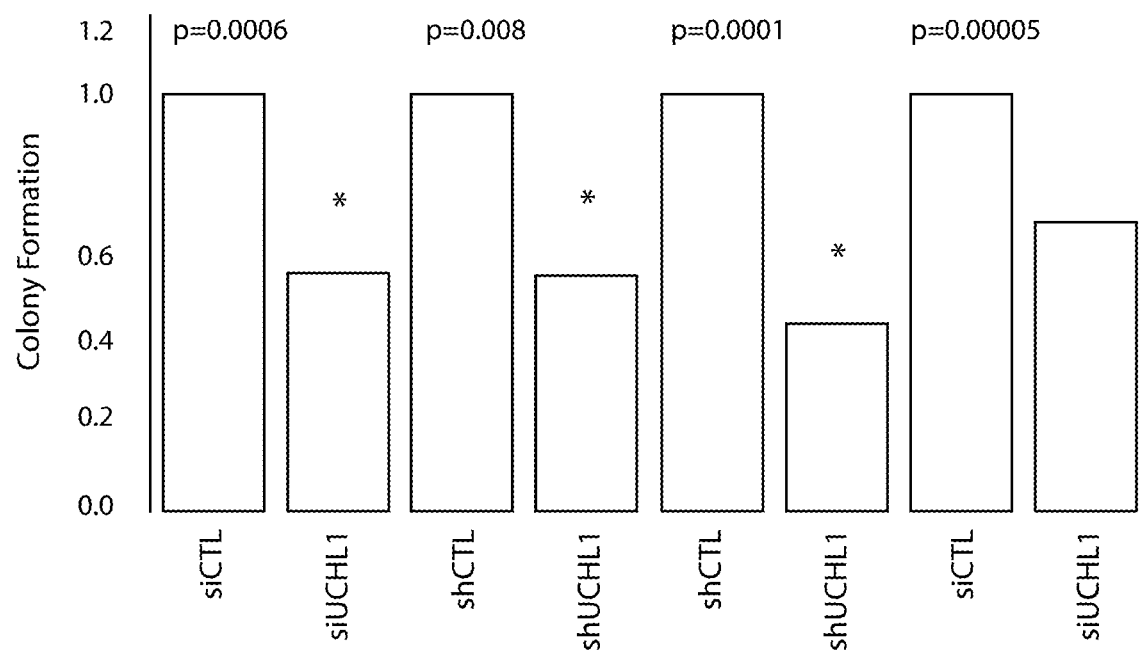
FIG. 8C depicts a significant decrease in colony formation at 8 and 10 days of UCHL1 silenced cells compared to unsilenced controls.

FIG. 8C depicts a significant decrease in colony formation at 8 and 10 days of UCHL1 silenced cells compared to unsilenced controls.

Figure 8D:
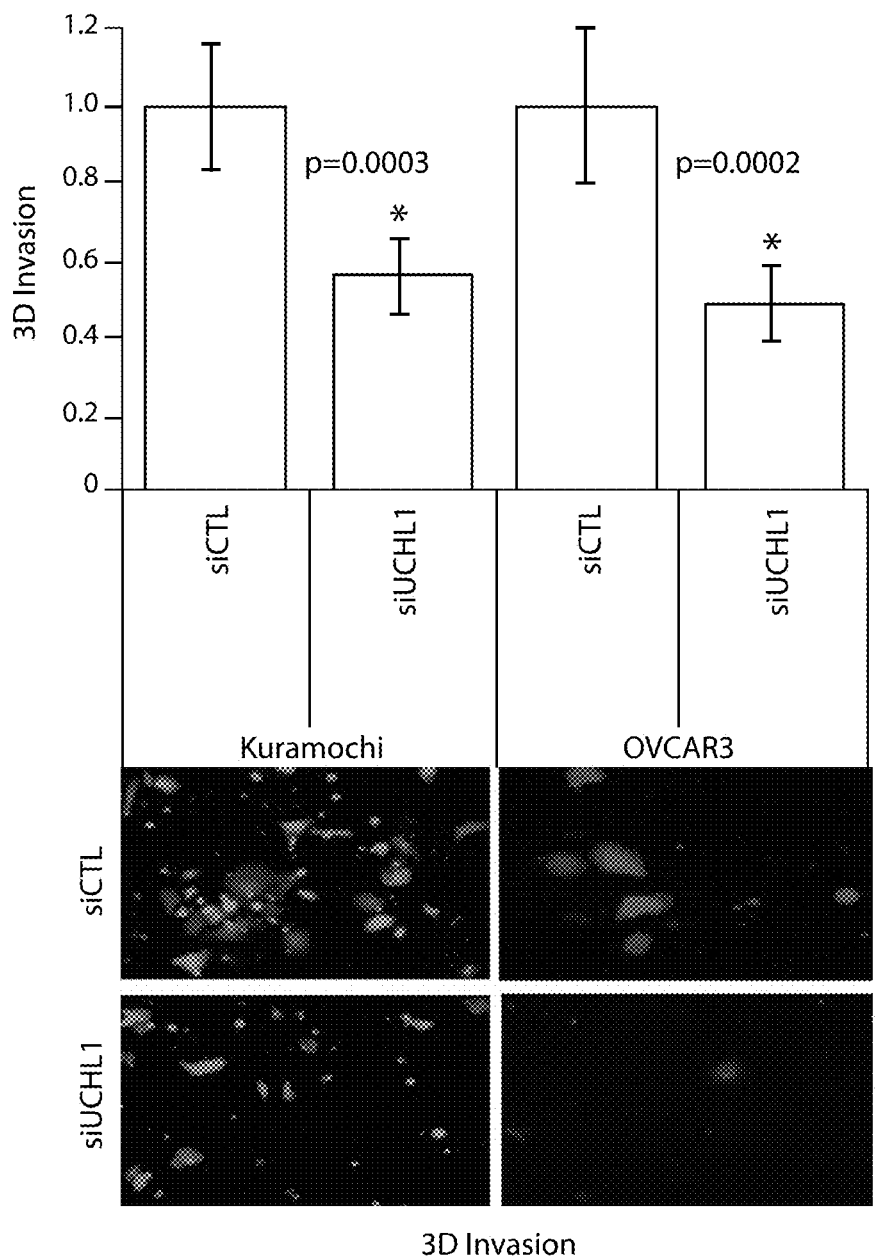
FIG. 8D depicts a significant decrease in three-dimensional invasion of UCHL1 silenced Kuramochi cells (GFP expressing) and OVCAR3 cells (RFP expressing) through layers of extracellular matrix, mesothelial cells, and fibroblasts isolated from the omentum of a healthy woman.

FIG. 8D depicts a significant decrease in three-dimensional invasion of UCHL1 silenced Kuramochi cells (GFP expressing) and OVCAR3 cells (RFP expressing) through layers of extracellular matrix, mesothelial cells, and fibroblasts isolated from the omentum of a healthy woman. The three-dimensional organotype model of ovarian cancer metastasis was set up in a transwell insert and the invaded fluorescent cancer cells were imaged after 6-8 hrs. This in vitro model of ovarian cancer metastasis mimics the metastasis to omentum in HGSOC patients.

EXAMPLE 7

Effect of Changes in UCHL1 Expression on Proteasome Subunit Alpha 7 Expression

Figure 9A:
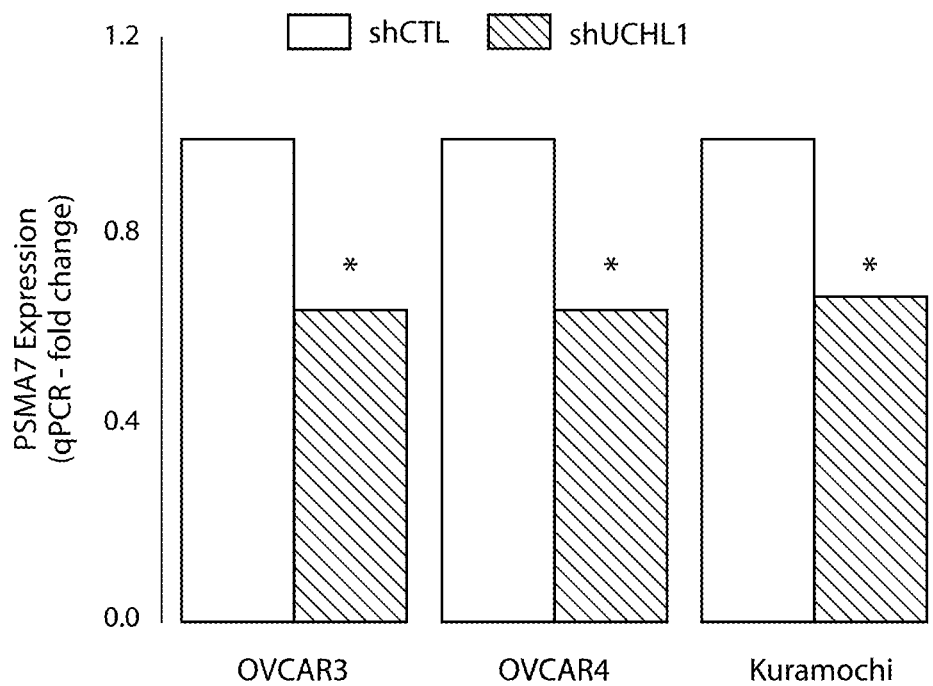
FIG. 9A depicts the reduction in proteasome subunit alpha 7 (PSMA7) expression in UCHL1 silenced Kuramochi, OVCAR3, and OVCAR4 cells.
Figure 9B:
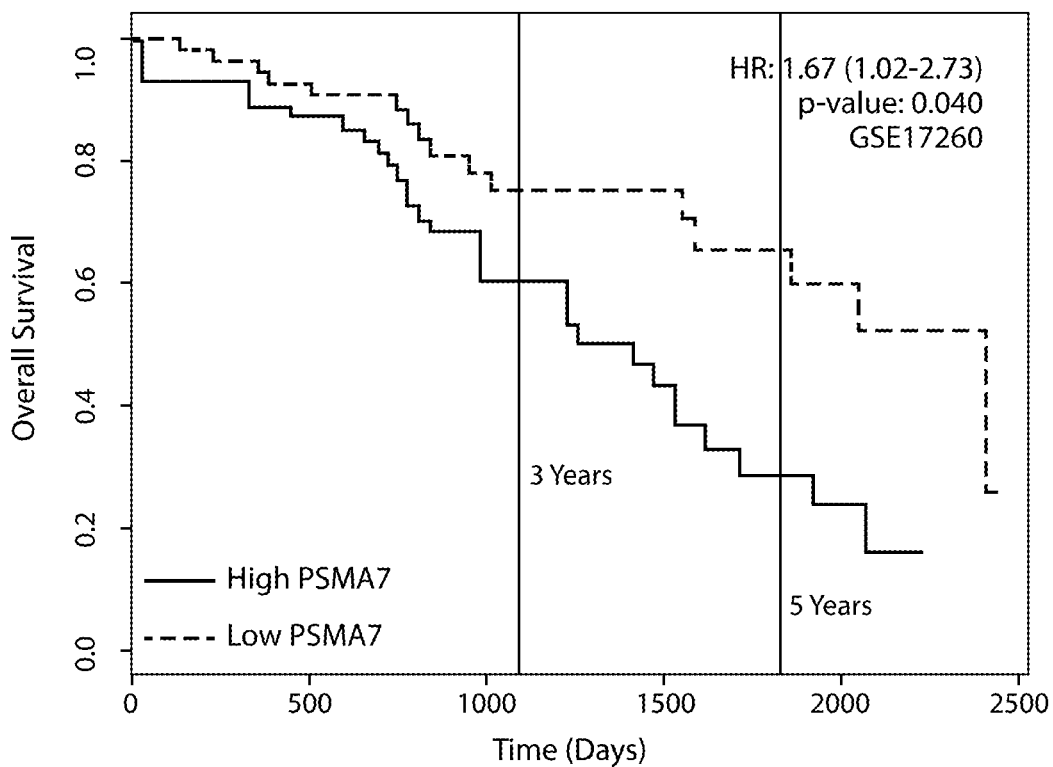
FIG. 9B depicts Kaplan Meier analysis showing improved survival of HGSOC patients with low PSMA7 level (PROG-geneV2).
Figure 10:
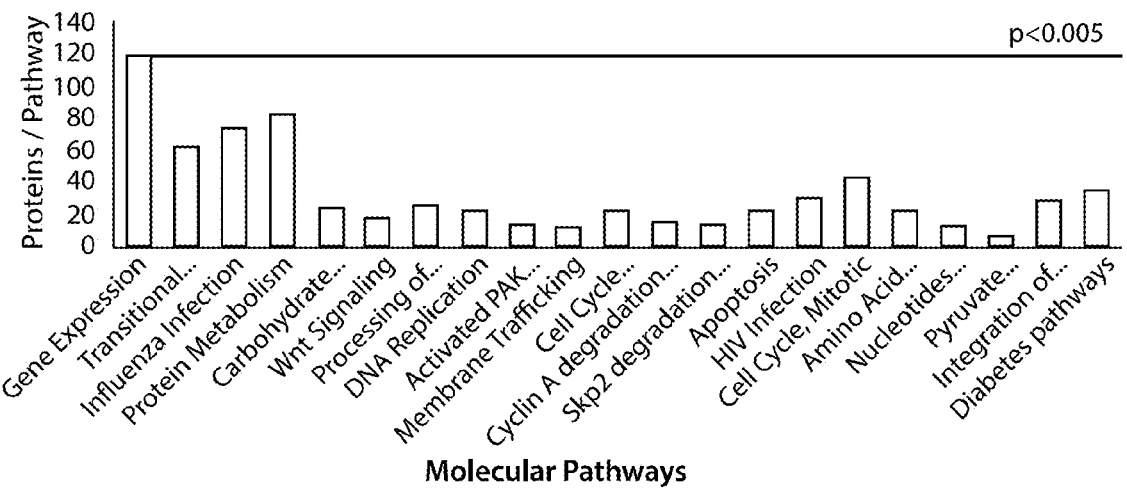
FIG. 10 shows results of a reactome pathway analysis using the Database for Annotation, Visualization and Integrated Discovery (DAVID), after liquid chromatography-mass spectrometry analysis of UCHL1-protein complex (UBHL1 immuno-precipitation) in Kuramochi cells. The shaded horizontal line indicates significant cut-off ($p<0.005$).

FIG. 9A depicts the reduction in proteasome subunit alpha 7 (PSMA7) expression in UCHL1 silenced Kuramochi, OVCAR3, and OVCAR4 cells. FIG. 9B depicts Kaplan Meier analysis showing improved survival of HGSOC patients with low PSMA7 level (PROGgeneV2). FIG. 9C depicts reduced viability of PSMA7 silenced HGSOC cells (MTT assay; day 3). As shown in FIG. 9D, the PSMA7 silenced OVCAR3 cells also demonstrated reduced proteasomal activity. FIG. 9E depicts a significant decrease in proteasomal activity in PSMA7 silenced Kuramochi and OVCAR3 cells. PSMA7 subunit of proteasomes is associated with increased proteasomal activity in yeast.

EXAMPLE 8

Transgenic Mouse Model of HGSOC

A transgenic mouse model of HGSOC expressing R172H gain-of-function p53 mutation was developed. The model exhibited increased UCHL1 levels in murine primary and metastatic tumors.

EXAMPLE 9

Effect of UCHL1 Inhibition on Growth and Progression of HGSOC Metastatic Tumors

Figure 11A:
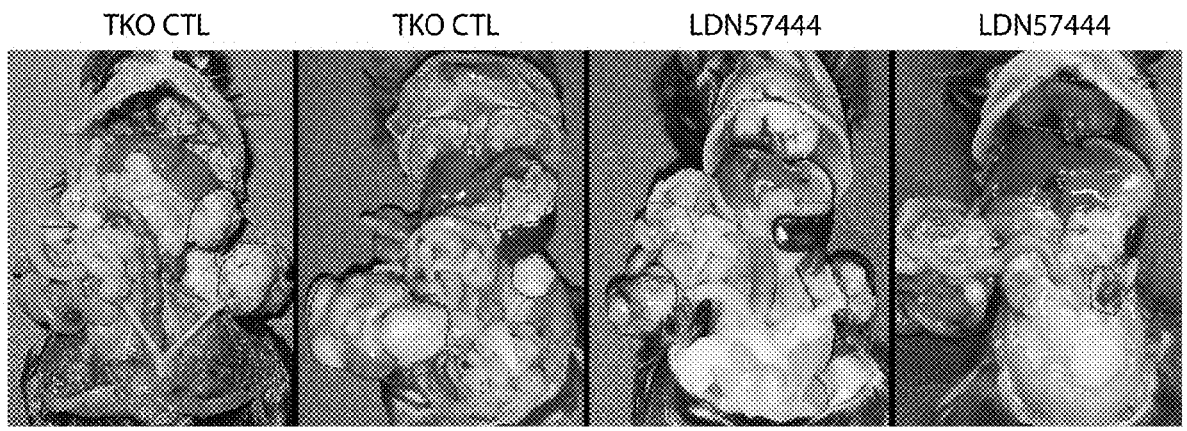
FIG. 11A shows partial dissection of TKO control mice and TKO mice after receiving treatment with LDN57444.

Triple mutant (TKO) mice are Pten and Dicer knockout and overexpress mutant p53 R172H (corresponding to human R175H mutant) (Pten−/− Dicer−/− and p53-R172H). These mice spontaneously developed primary tumors in the fallopian tube at age 4 months, which metastasize to other organs by 5-6 months. This model recapitulates metastatic tumor growth as in ovarian cancer patients. FIG. 11A shows photographs of TKO Control (CTL) mouse tumors in peritoneal wall, ovary, omentum, mesentery (intestine), and diaphragm. The tumors are circled using a dotted line and/or indicated with arrows. The LDN5744 mice showed visible reduction in primary tumor (indicated with dotted line) and absence of metastatic tumors in the omentum, diaphragm, mesentery, and peritoneal wall (indicated with arrows).

Figure 11B:
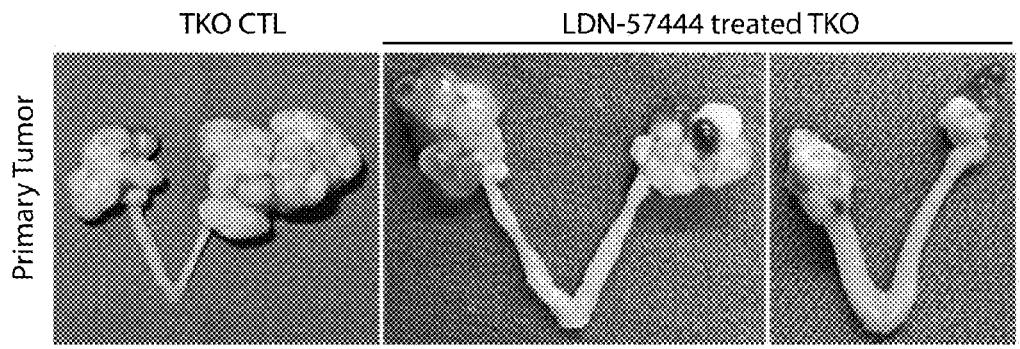
FIG. 11B illustrates the reduction in primary HGSOC tumor size with LDN treatment in mice aged 4-6 months.
Figure 11C:
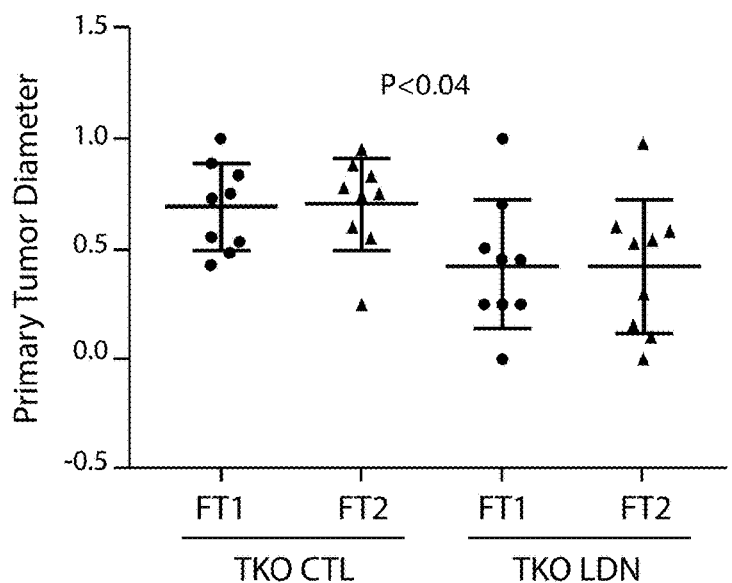
FIG. 11C illustrates the reduction in primary HGSOC tumor size with LDN treatment in mice aged 4-6 months.

FIGS. 11B and 11C illustrate the reduction in primary HGSOC tumor size with LDN treatment in mice aged 4-6 months.

Figure 11D:
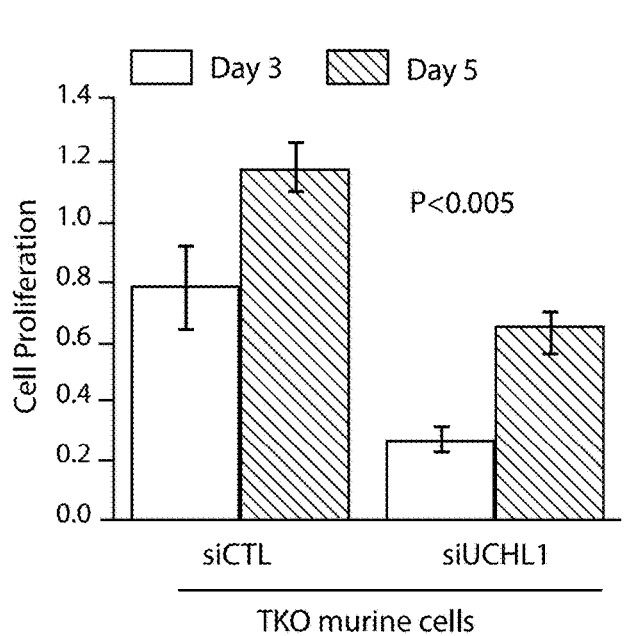
FIG. 11D is a cell proliferation analysis of silenced UCHL1 TKO cells.
Figure 11E:
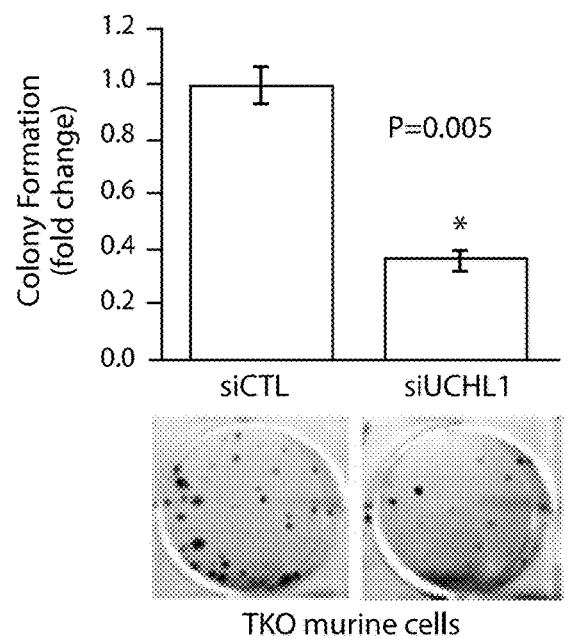
FIG. 11E is a colony formation analysis of silenced UCHL1 TKO cells.

In a further experiment, cells cultured from TKO mouse tumors were silenced for UCHL1 in vitro. Significant reduction in cellular proliferation (5-day and 3-day) in UCHL1 silenced TKO cells was observed compared to unsilenced controls. FIG. 11D illustrates these results. A significant decrease in clonogenicity of UCHL1 silenced TKO cells (colony forming assay at 8 and 10 days) was also observed compared to unsilenced controls. FIG. 11E is a colony formation analysis of silenced UCHL1 TKO cells.

EXAMPLE 10

In accordance with a method of the present invention, a patient with cancer is tested for the level of expression of UCHL1; upon detection of an elevated expression of UCHL1, a pharmaceutically effective amount of a ubiquitin carboxyl-terminal hydrolase inhibitor is administered to the patient. In a further embodiment a chemotherapeutic agent is also administered to the patient.

In accordance with a method of the present invention, a patient with cancer is tested for the presence of a gain of function p53 mutation; upon detection of a gain of function p53 mutation, a pharmaceutically effective amount of a ubiquitin carboxyl-terminal hydrolase inhibitor is administered to the patient. In a further embodiment a chemotherapeutic agent is also administered to the patient.

In accordance with a method of the present invention, ubiquitin carboxyl-terminal hydrolase inhibitor is used in the manufacture of a medicament for the treatment of cancer.

EXAMPLE 11

Mechanism of UCHL1 Mediated Cancer Growth and Progression

RNA-sequencing data was collected showing both the upregulated (orange color) and downregulated genes in UCHL1 silenced Kuramochi cells compared to unsilenced controls. FIG. 12A illustrated these results. Proteasomal subunit alpha 7 (PSMA7) gene was among the top dysregulated genes in the RNA-sequence analysis.

QPCR validation was performed for reduced PSMA7 expression in UCHL1 silenced OVCAR3, OVCAR4, and Kuramochi HGSOC cells. These results are illustrated at FIG. 12B. FIG. 12C illustrates increased PSMA7 expression in HGSOC patients primary tumor compared to normal ovary. FIG. 12D illustrates survival analysis of HGSOC patients. The analysis demonstrates poor overall survival and progression free survival of patients with elevated PSMA7 levels (log rank p=0.007 and 0.03).

The TKO mice were treated with UCHL1 inhibitor, LDN-57444. The treated mice showed reduced PSMA7 RNA and protein levels compared to untreated TKO Control (CTL) mice. Proteasome activity was significantly reduced in LDN-57444 treated mice compared to TKO CTL mice. The results of this analysis are illustrated in FIG. 12E.

The many features and advantages of the invention are apparent from the detailed specification, and thus, it is intended by the appended claims to cover all such features and advantages of the presently disclosed patient matter which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

While the presently disclosed patient matter has been disclosed with reference to certain embodiments, numerous modifications, alterations, and changes to the described embodiments are possible without departing from the sphere and scope of the presently disclosed patient matter, as defined in the appended claims. Accordingly, it is intended that the presently disclosed patient matter not be limited to the described embodiments, but that it has the full scope defined by the language of the following claims, and equivalents thereof.

What is claimed is:

1. A method for treatment of high-grade serous ovarian cancer associated with a mutation of a p53 gene, comprising: administering a pharmaceutically effective amount of a ubiquitin carboxyl-terminal hydrolase inhibitor to a patient with high-grade serous ovarian cancer associated with a mutation of a p53 gene, wherein ubiquitin carboxyl-terminal hydrolase L1 (UCHL1) is overexpressed and the ubiquitin carboxyl-terminal hydrolase inhibitor is effective to inhibit UCHL1 in the high-grade serous ovarian cancer.

2. The method of claim 1, further comprising: detecting overexpression of UCHL1 in the patient prior to administration of the ubiquitin carboxyl-terminal hydrolase inhibitor.

3. The method of claim 1, further comprising administering a chemotherapeutic agent to the patient.

4. The method of claim 1, further comprising: detecting the presence of a p53 mutation in the patient prior to administering ubiquitin carboxyl-terminal hydrolase inhibitor.

* * * * *